(12) United States Patent
Tajima et al.

(10) Patent No.: US 6,621,093 B2
(45) Date of Patent: Sep. 16, 2003

(54) IMAGE SCANNING APPARATUS

(75) Inventors: Kenji Tajima, Odawara (JP); Kenji Takata, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/795,080

(22) Filed: Mar. 1, 2001

(65) Prior Publication Data

US 2001/0019113 A1 Sep. 6, 2001

(30) Foreign Application Priority Data

Mar. 1, 2000 (JP) ........................ 2000-056425
Mar. 24, 2000 (JP) ........................ 2000-083889
Mar. 24, 2000 (JP) ........................ 2000-083898

(51) Int. Cl.[7] .............................................. G03B 42/02
(52) U.S. Cl. ...................... 250/582; 250/589; 250/590; 378/189
(58) Field of Search ................................. 250/582, 584, 250/586, 588, 589, 590; 378/208, 209, 189; 5/601

(56) References Cited

U.S. PATENT DOCUMENTS

| 3,681,792 A | * | 8/1972 | Korber ............................ 5/618 |
| 4,762,999 A | * | 8/1988 | Saotome et al. ............. 250/589 |
| 4,827,128 A | * | 5/1989 | Nakajima .................... 250/589 |
| 5,297,539 A | * | 3/1994 | Liebl et al. ..................... 601/26 |

* cited by examiner

Primary Examiner—Constantine Hannaher
Assistant Examiner—Shun Lee
(74) Attorney, Agent, or Firm—Sughrue Mion, PLLC

(57) ABSTRACT

An image scanning apparatus has an imaging bed for placing a subject thereon, the imaging bed having a recording unit for temporarily recording radiation image information of the subject on a stimulable phosphor sheet, a housing accommodating therein a reading unit for photoelectrically reading the radiation image information from the stimulable phosphor sheet, and an erasing assembly for erasing remaining radiation image information from the stimulable phosphor sheet, and a lifting/lowering mechanism for lifting and lowering the imaging bed with respect to the housing. The subject can easily be put onto the imaging bed, and the imaging bed can easily be operated.

14 Claims, 18 Drawing Sheets

IMAGE SCANNING APPARATUS

BACKGROUND OF THE INVENTION

1. Field of the Invention

The present invention relates to an image scanning apparatus for recording and reading radiation image information of a subject on and from a stimulable phosphor sheet.

2. Description of the Related Art

There is known a system for recording radiation image information of a subject such as a human body with a stimulable phosphor, and reproducing the recorded radiation image information on a photosensitive medium such as a photographic film, or displaying the recorded radiation image information on a display device such as a CRT or the like.

When a radiation energy such as X-rays, α-rays, γ-rays, electron beams, ultraviolet radiation, or the like is applied to a certain phosphor, it stores part of the applied radiation energy. When stimulating light such as visible light is subsequently applied to the phosphor, the phosphor emits light depending the stored radiation energy. Such a phosphor is referred to as a stimulable phosphor. A stimulable phosphor is usually used in the form of a sheet which is referred to as a stimulable phosphor sheet, for the ease with which it can be handled.

The above known system comprises a built-in radiation image information reading apparatus which includes a recording section for temporarily recording radiation image information of a subject on a stimulable phosphor sheet, a reading section for photoelectrically reading the radiation image information recorded on the stimulable phosphor sheet by applying simulating light to the stimulable phosphor sheet, and an erasing section for erasing remaining radiation image information from the stimulable phosphor sheet after the recorded radiation image information has been read, the stimulable phosphor sheet being circulated or moved back and forth in the apparatus.

One known type of the built-in radiation image information reading apparatus has an imaging bed that is horizontally movable. For example, as shown in FIG. 18 of the accompanying drawings, a conventional radiation image information reading apparatus 1 has a housing 2 and an imaging bed 3 floatingly supported on the top of the housing 2 for movement along two horizontal axes, i.e., X- and Y-axes. A patient 4, who is a subject to be imaged, lies on the imaging bed 3, with the back down, as shown, or one side down.

The operator 5 moves the imaging bed 3 along the X-axis or the Y-axis to bring a desired imaging area of the patient 4 into registration with the X-ray applying position of an X-ray radiating unit 6. Then, the operator 5 energizes the X-ray radiating unit 6 to capture radiation image information of the desired imaging area of the patient 4.

The height H of the imaging bed 3 is set to a vertical position that is suitable for the operator 5 to operate the radiation image information reading apparatus 1 efficiently. If the patient 4 is of a small height, then the operator 5 needs to provide a step for the patient 4 to use because the patient 4 would otherwise find it difficult to climb on the imaging bed 3. Furthermore, if the patient 4 is delivered on a wheelchair or a stretcher, then it is highly laborious and time-consuming to transfer the patent 4 from the wheelchair or the stretcher onto the imaging bed 3.

SUMMARY OF THE INVENTION

It is therefore an object of the present invention to provide an image scanning apparatus which allows a subject to be easily placed on an imaging bed and permits the operator to operate the imaging bed with ease.

A major object of the present invention is to provide an image scanning apparatus which is capable of smoothly and reliably guiding a scanned body to feed the scanned body stably when a feed path is extended.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
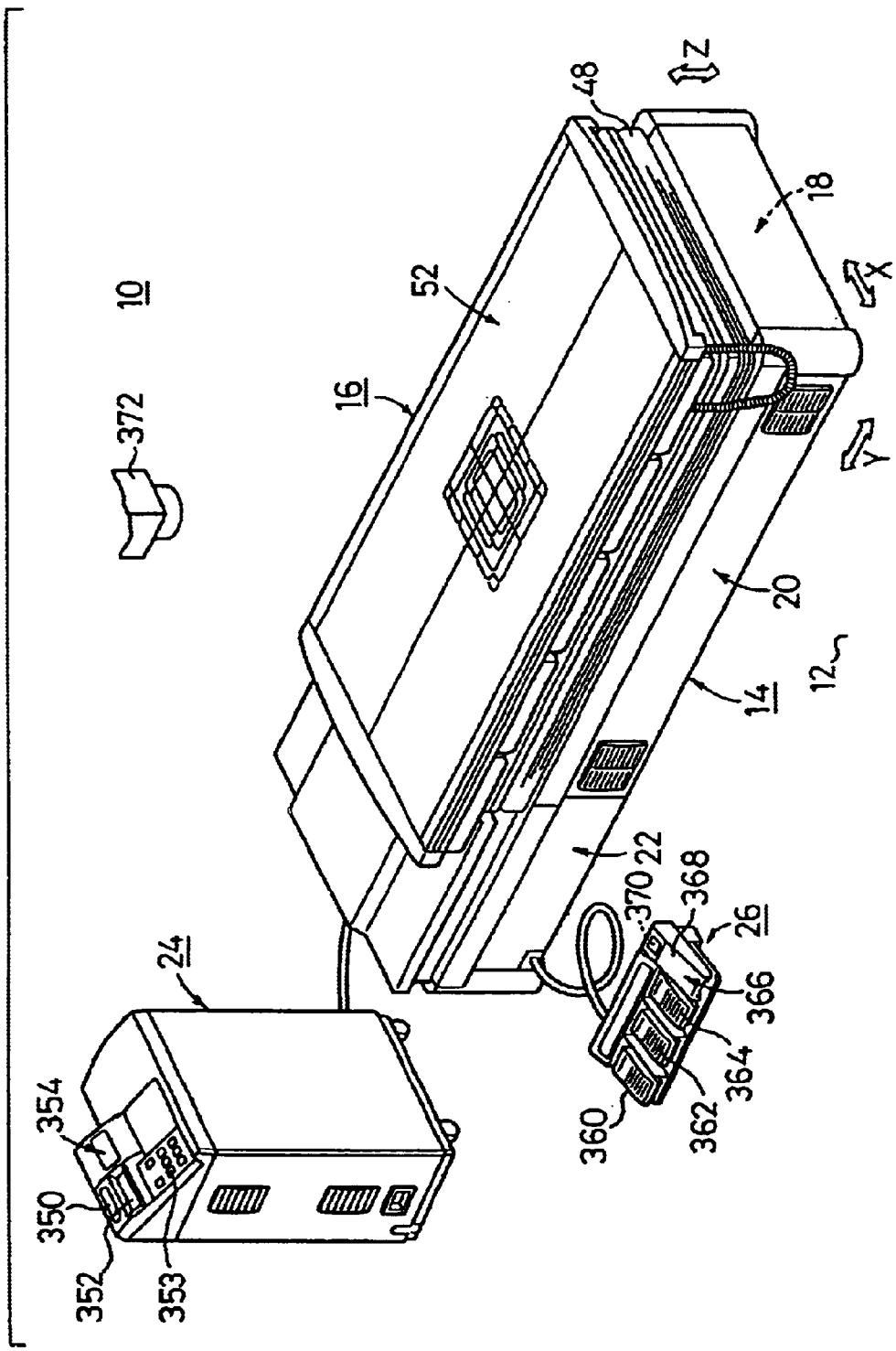
FIG. 1 is a perspective view of a radiation image information reading apparatus as an image scanning apparatus according to the present invention.
Figure 2:
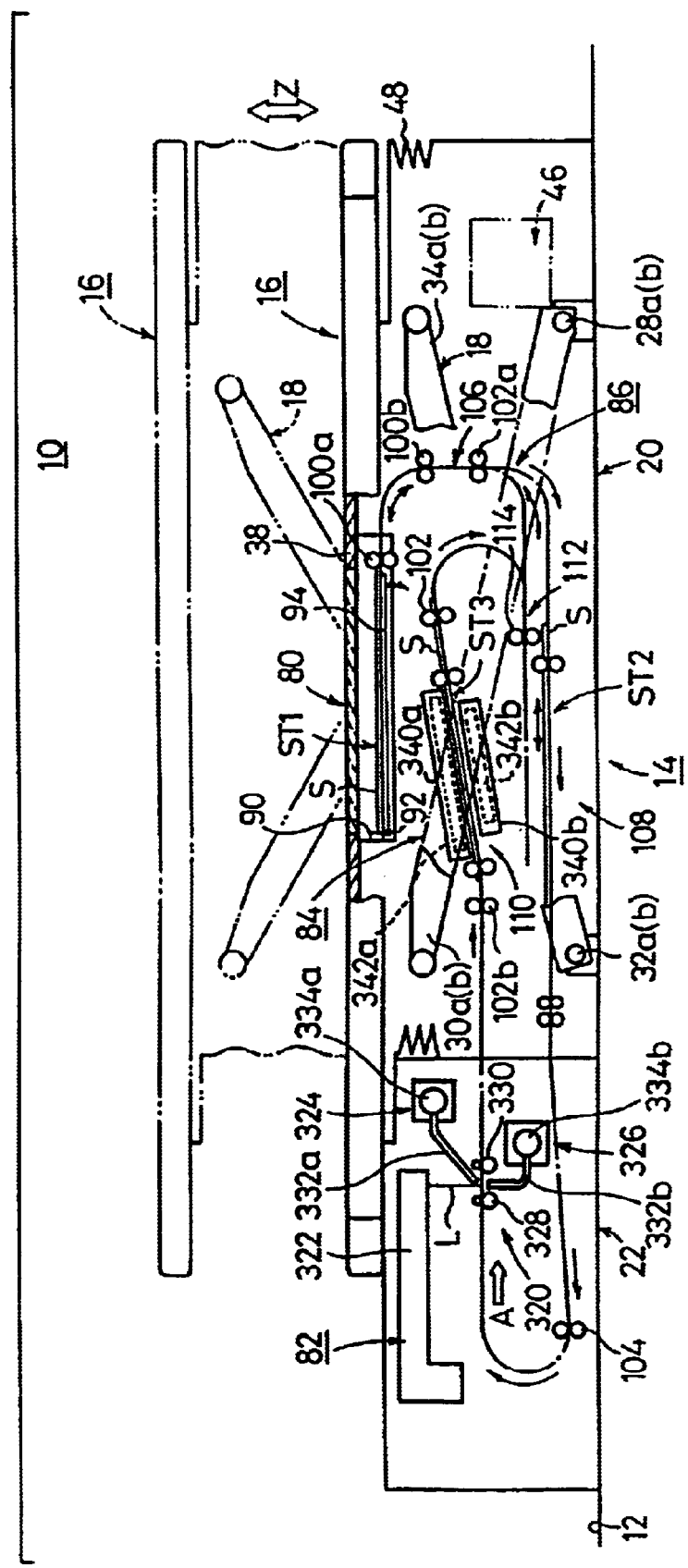
FIG. 2 is a schematic side elevational view showing an internal structure of the radiation image information reading apparatus.

As shown in FIGS. 1 and 2, a radiation image information reading apparatus 10, which serves as an image reading apparatus according to the present invention, comprises a housing 14 placed on a floor or installation surface 12, an imaging bed 16 for supporting a patient, with the back or one side down, directly thereon, and a lifting/lowering mechanism 18 for lifting and lowering the imaging bed 16 with respect to the housing 14. The housing 14 comprises a first casing 20 housing the lifting/lowering mechanism 18 therein and a second casing 22 separate from and adjacent to the first casing 20. A controller 24 and a switch unit 26 are connected to the second casing 22.

Figure 3:
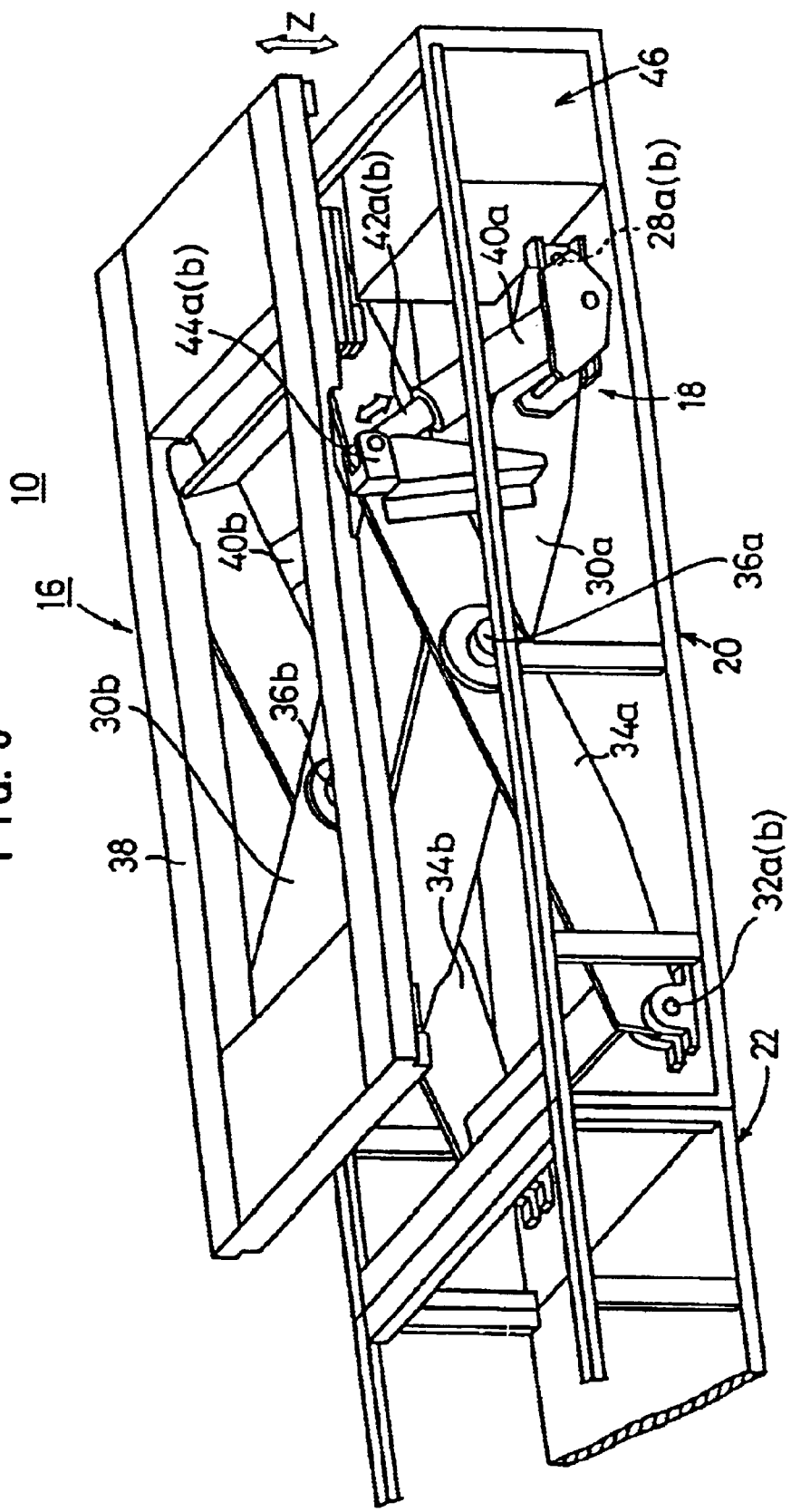
FIG. 3 is a perspective view of an internal structure of a first casing and an imaging bed of the radiation image information reading apparatus.

As shown in FIGS. 2 and 3, the lifting/lowering mechanism 18 comprises a pair of horizontally spaced first swing arms 30a, 30b swingably supported on one end of the first casing 20 remote from the second casing 22 by respective pivot shafts 28a, 28b, and a pair of horizontally spaced second swing arms 34a, 34b swingably supported on the opposite end of the first casing 20 close to the second casing 22 by respective pivot shafts 32a, 32b. The first and second swing arms 30a, 34a and the first and second swing arms 30b, 34b are coupled to each other by respective joint shafts 36a, 36b at substantially central regions thereof. The first swing arms 30a, 30b and the second swing arms 34a, 34b have respective distal ends held in operative engagement with the bottom of a vertically movable base 38 of the imaging bed 16.

First and second hydraulic cylinders 40a, 40b are mounted respectively on the first swing arms 30a, 30b near the pivot shafts 28a, 28b and have respective rods 42a, 42b extending toward and coupled to the second swing arms 34a, 34b, respectively, by attachments 44a, 44b near upper ends of the second swing arms 34a, 34b. The first and second hydraulic cylinders 40a, 40b are controlled by a hydraulic unit 46 mounted in the first casing 14.

Figure 4:
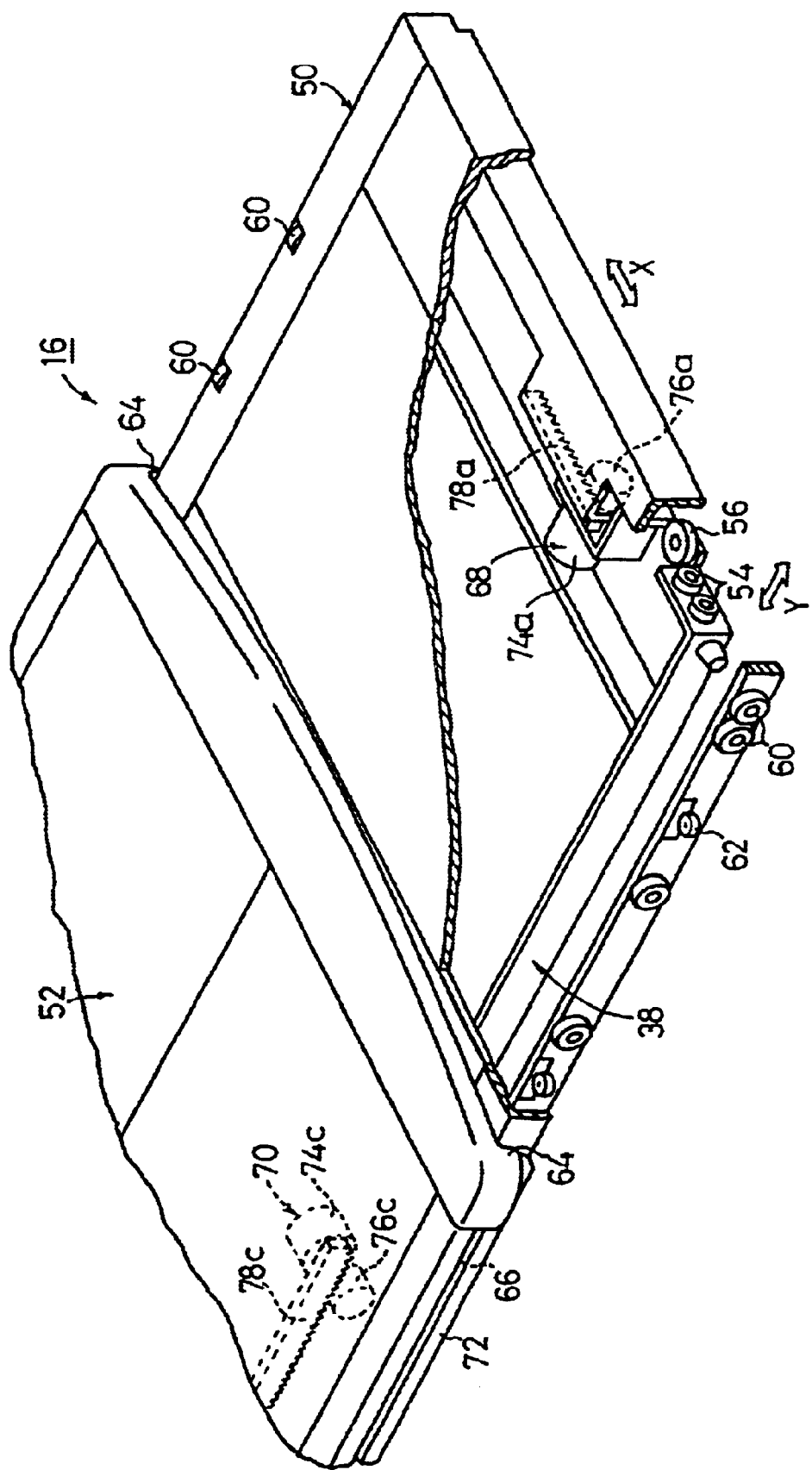
FIG. 4 is a fragmentary perspective view, partly broken away, of the imaging bed.

As shown in FIG. 1, a dust-resistant, light-shielding bellows 48 which is vertically expandable and contractible is disposed between and connected to the vertically movable base 38 and the first casing 20. As shown in FIG. 4, a movable table 50 that can be displaced in the transverse directions of the first casing 20 indicated by the arrow X is mounted on the vertically movable base 38, and a top panel 52 movable in the longitudinal directions indicated by the arrow Y, perpendicular to the directions indicated by the arrows X, is mounted on the movable table 50.

A plurality of rollers 54 rotatable about respective horizontal axes and a guide roller 56 rotatable about a vertical axis are mounted on each of the opposite ends of the vertically movable base 38 in the directions indicated by the arrow Y. The movable table 50 is in the form of a frame having, on each of its opposite ends, a guide 58 of channel-shaped cross section in which the rollers 54 and the guide roller 56 are rollingly supported. A plurality of rollers 60 rotatable about respective horizontal axes and a plurality of guide rollers 62 rotatable about respective vertical axes are mounted on each of the opposite ends of the movable table 50 in the directions indicated by the arrow X.

The top panel 52 has a pair of guides 64 of channel-shaped cross section on the respective ends thereof in the directions indicated by the arrow X, and the rollers 60 and the guide rollers 62 are rollingly supported in the guides 64. Two linear touch switches 66 are fixed to the respective ends of the top panel 52 along the respective guides 64. The touch switches 66 are used to turn on and off first and second lock units 68, 70 which lock the movable table 50 and the top panel 52. While one of the touch switches 66 is being pressed, the first and second lock units 68, 70 unlock the movable table 50 and the top panel 52. Protective covers 72 are mounted on the top panel 52 outwardly of the respective touch switches 66.

Figure 5:
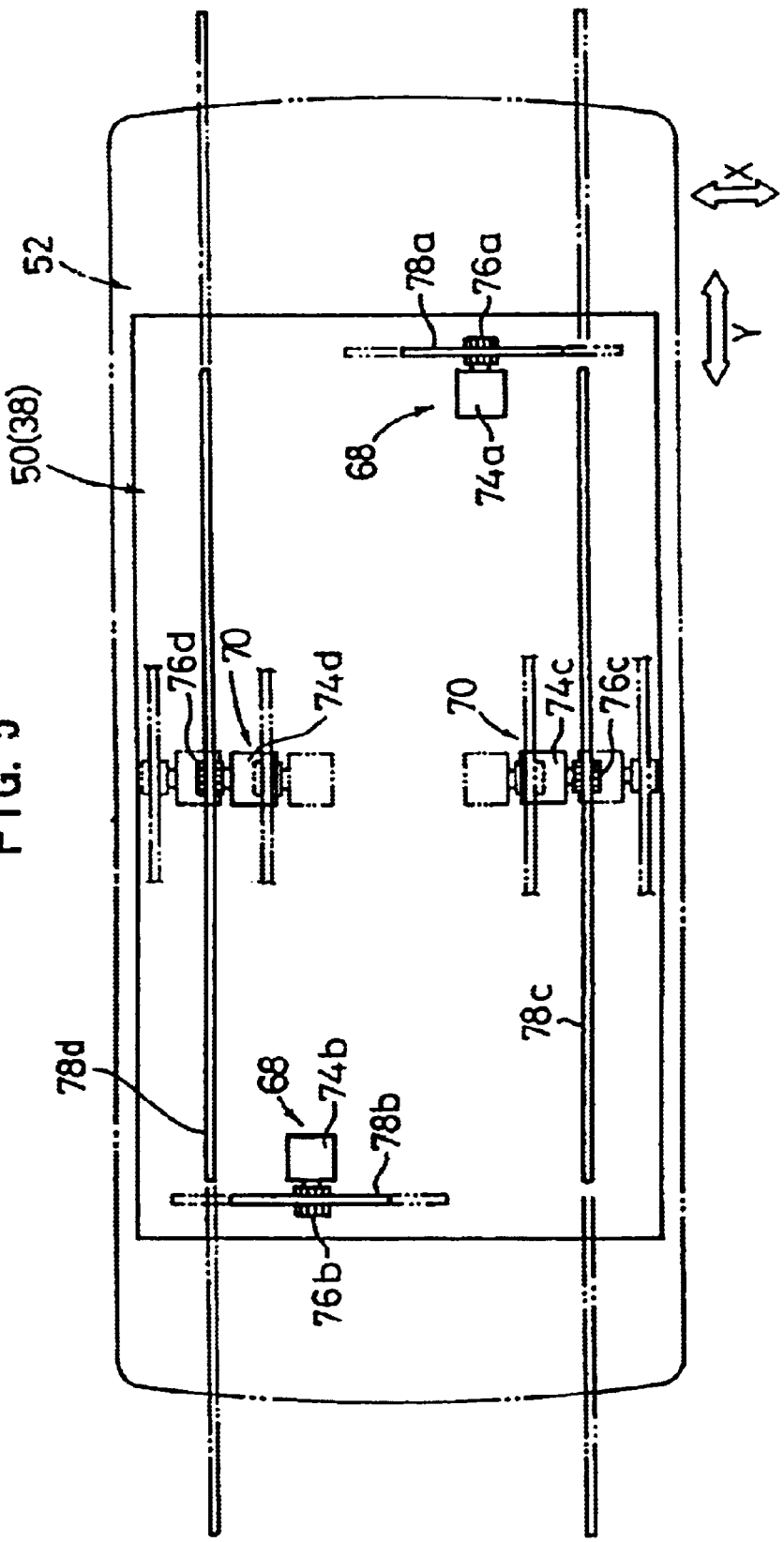
FIG. 5 is a plan view of first and second lock units of the imaging bed.

As shown in FIGS. 4 and 5, the first lock unit 68 comprises a pair of electromagnetic brakes 74a, 74b fixedly positioned at the opposite ends of the vertically movable base 38 in the directions indicated by the arrow Y in point symmetry relationship to each other, a pair of pinion gears 76a, 76b secured to the respective electromagnetic brakes 74a, 74b, and a pair of racks 78a, 78b extending in the directions indicated by the arrow X and fixed to the movable table 50, the racks 78a, 78b being held in mesh with the pinion gears 76a, 76b. The second lock unit 70 comprises a pair of electromagnetic brakes 74c, 74d fixedly positioned at the opposite ends of the movable table 50 in the directions indicated by the arrow X in symmetrical relationship to each other, a pair of pinion gears 76c, 76d secured to the respective electromagnetic brakes 74c, 74d, and a pair of racks 78c, 78d extending in the directions indicated by the arrow Y and fixed to the top plate 52, the racks 78c, 78d being held in mesh with the pinion gears 76c, 76d.

As shown in FIG. 2, the vertically movable base 38 supports therein a recording unit 80 for temporarily recording radiation image information of a subject on a stimulable phosphor sheet S. The housing 14 houses therein a reading unit 82 for photoelectrically reading the image information recorded on the stimulable phosphor sheet S by applying a laser beam L as simulating light to the stimulable phosphor sheet S, an erasing assembly 84 for erasing remaining radiation image information from the stimulable phosphor sheet S after the recorded image information has been read, and a circulating feed system 86 for circulating three stimulable phosphor sheets S, for example, in the image information reading apparatus 10.

Figure 6:
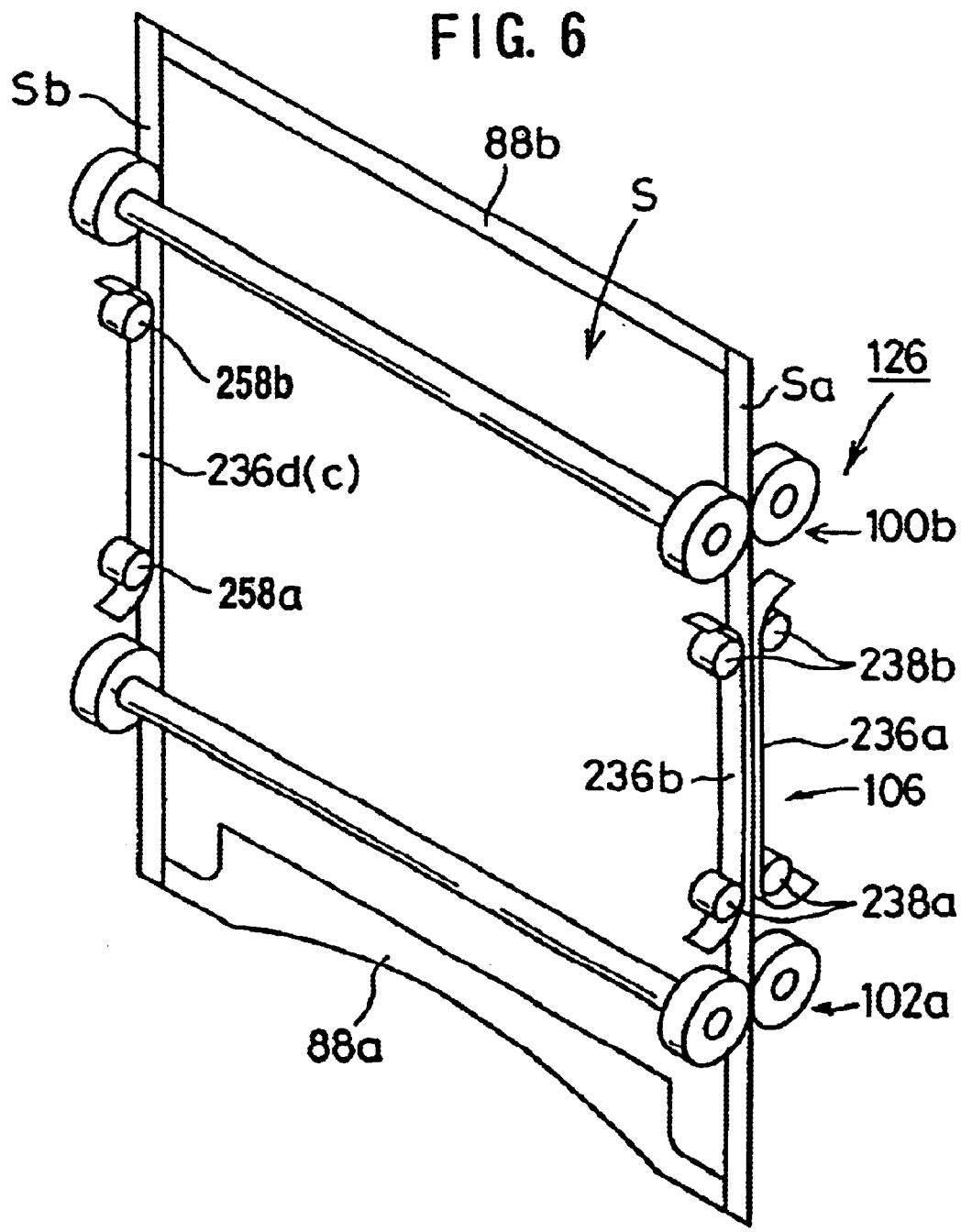
FIG. 6 is a perspective view of a stimulable phosphor sheet.

As shown in FIG. 6, the stimulable phosphor sheet S is gripped only at its opposite marginal edges Sa, Sb when it is fed in circulation. Reinforcing plates 88a, 88b are fixed to the reverse side of the stimulable phosphor sheet S.

As shown in FIG. 2, the recording unit 80 has a positioning member 90 for positioning the stimulable phosphor sheet S in an imaging position, and a holder plate 94 swingable about a pivot 92 for holding the stimulable phosphor sheet S in position in the recording unit 80. The circulating feed system 86 has a roller pair 100a disposed near an inlet/outlet end of the recording unit 80 remote from the positioning member 90, and a roller pair 100b spaced a given distance from the roller pair 100a. The roller pairs 100a, 100b are supported on the vertically movable base 38 for vertical movement in unison with the vertically movable base 38.

The circulating feed system 86 also has a plurality of roller pairs 102 disposed in the first casing 20. The second casing 22 houses therein a roller pair 104 which is independent of the circulating feed system 86. The roller pairs 102 include a roller pair 102a and a plurality of roller pairs 102b. The roller pairs 100a, 100b, 102a, 102b, 104 grip only the marginal edges Sa, Sb of the stimulable phosphor sheet S to feed the stimulable phosphor sheet S.

The circulating feed system 86 comprises a vertical feed path 106 extending vertically downwardly from the recording unit 80, a horizontal feed path 108 extending horizontally from the lower end of the vertical feed path 106 to the roller pair 104, an inclined feed path 110 turning 1800 back from the roller pair 104 and extending through the reading unit 82 to a position beyond the erasing assembly 84, and a switchback feed path 112 turning 1800 back from the tip end of the inclined feed path 110 for sheet switchback and joined to the vertical feed path 106. The circulating feed system 86 includes a reversible roller pair 114 disposed at the switchback feed path 112.

Figure 7:
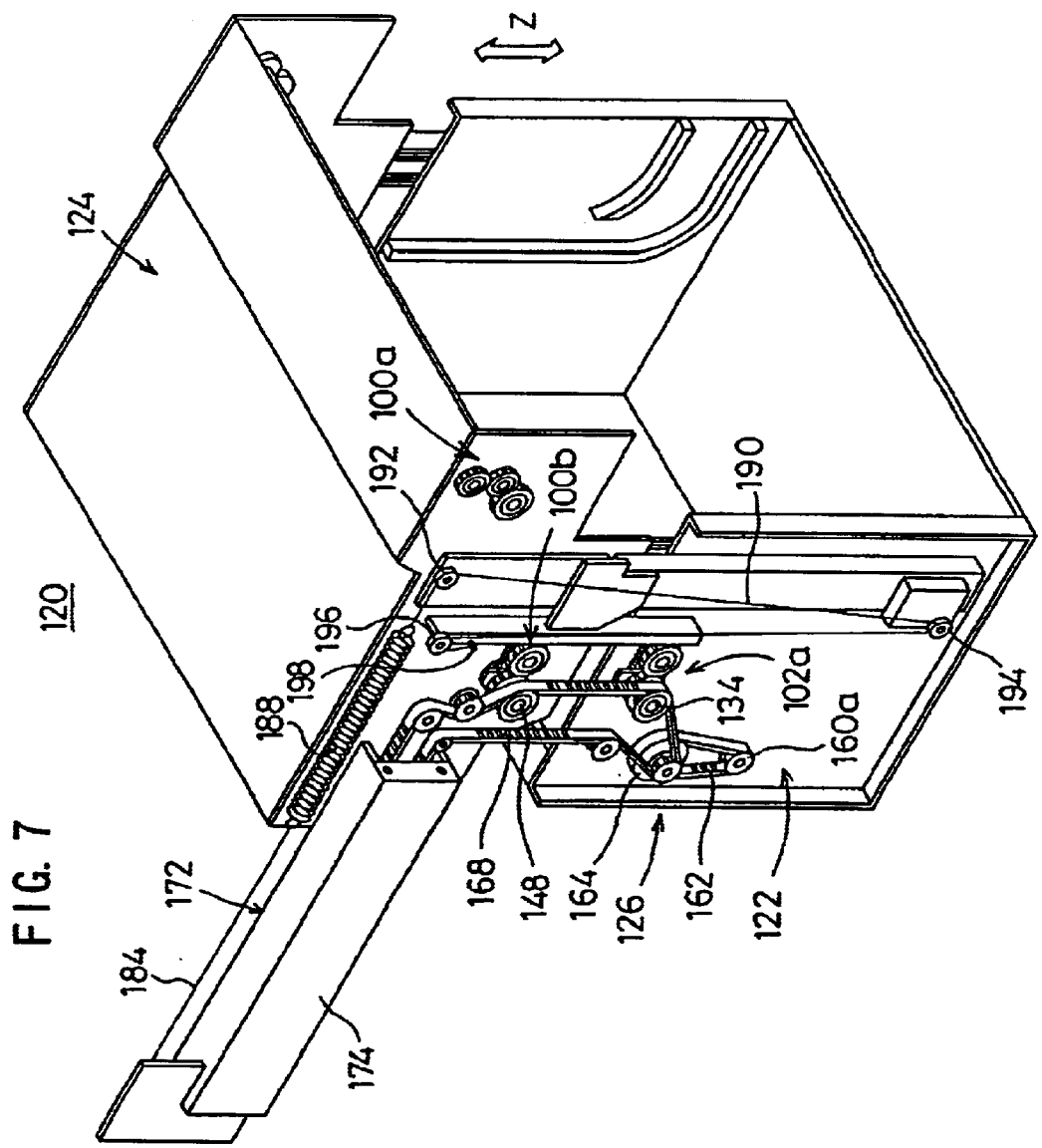
FIG. 7 is a perspective view of a feed device.
Figure 8:
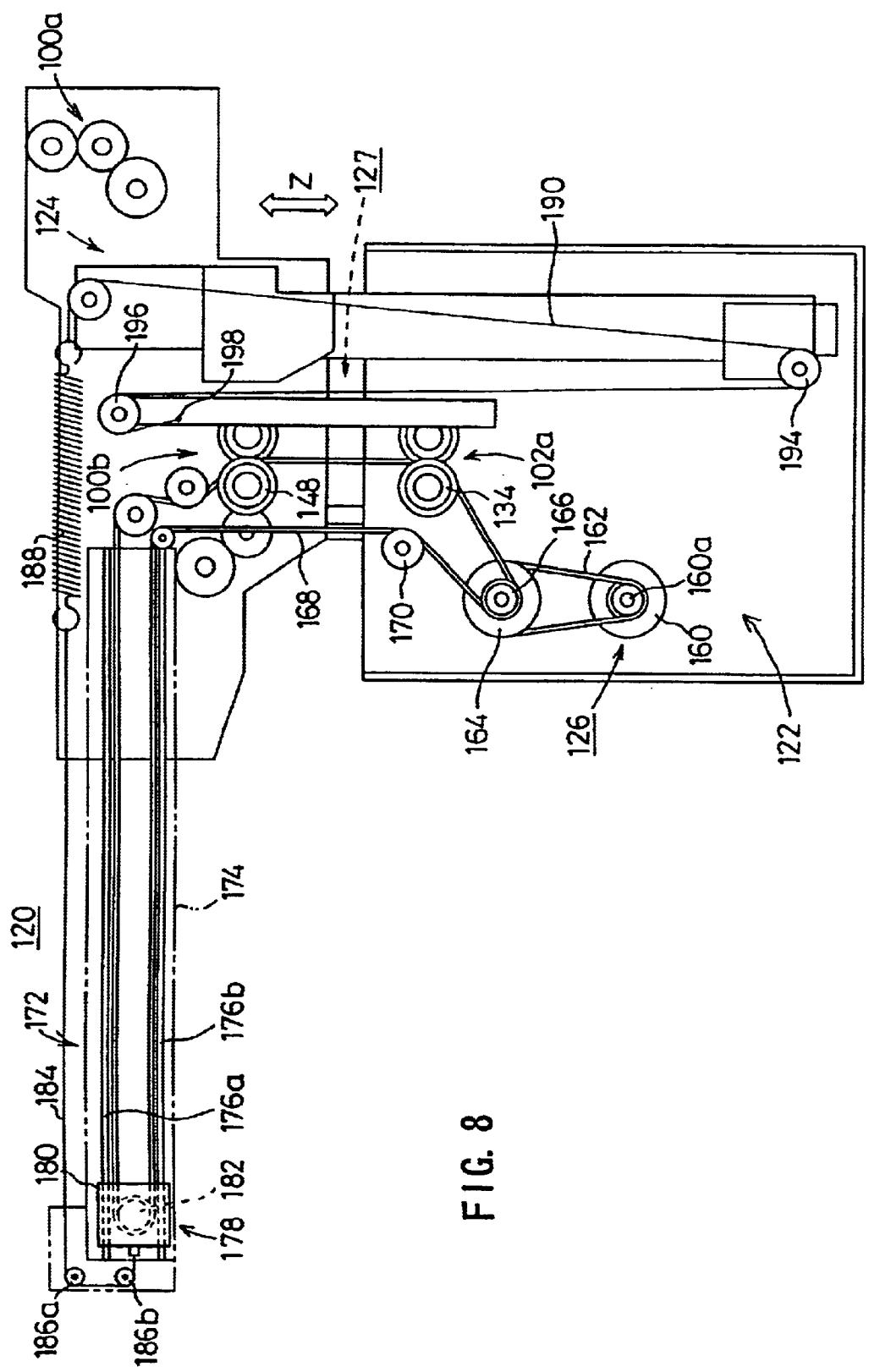
FIG. 8 is a side elevational view of the feed device.

The vertical feed path 106 can be extended and contracted between the roller pairs 100b, 102a when the imaging bed 16 is vertically moved. The vertical feed path 106 incorporates a feed device 120 therein. As shown in FIGS. 7 and 8, the feed device 120 comprises a fixed roller pair 102a rotatably supported on a fixed base 122 that is fixed to the first casing 20, a movable roller pair 100b rotatably supported on a movable base 124 fixed to the vertically movable base 38 and movable toward and away from the fixed base 122 so that the distance between the movable roller pair 100b and the fixed roller pair 102a can be varied, a drive mechanism 126 for rotating the roller pairs 102a, 100b in unison with each other, and a guide mechanism 127 for guiding the stimulable phosphor sheet S along the vertical feed path 106.

Figure 9:
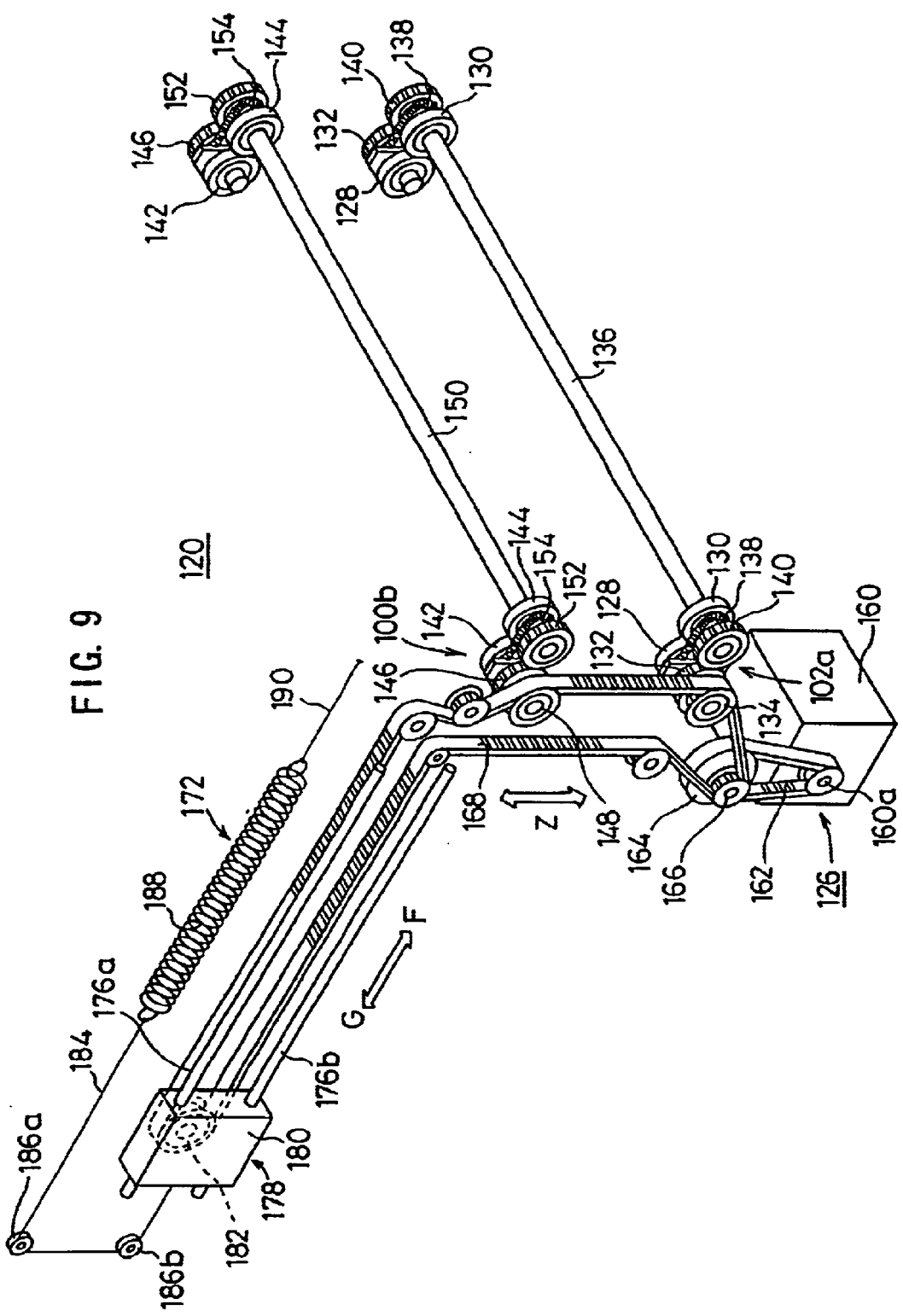
FIG. 9 is a perspective view of a portion of the feed device.
Figure 10:
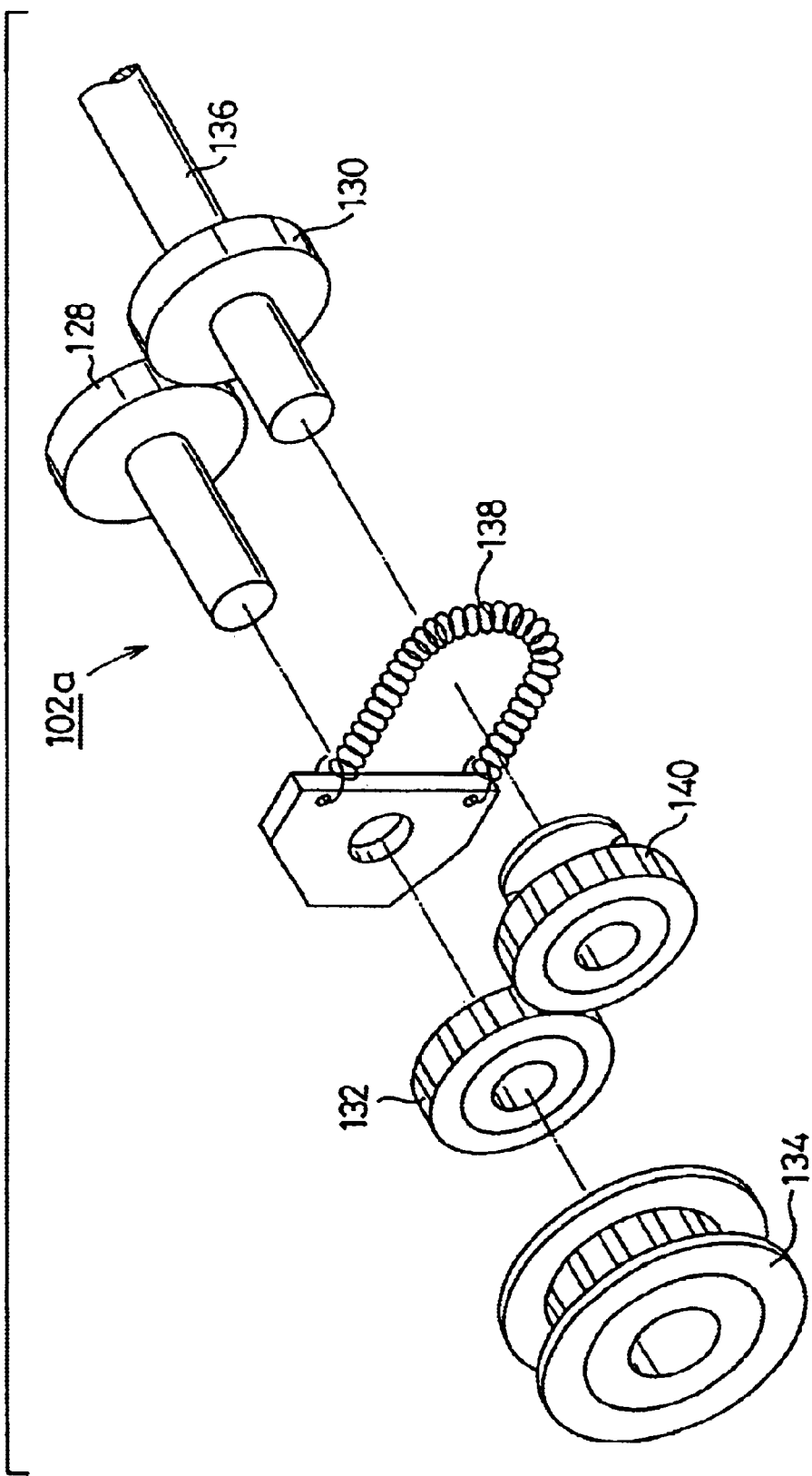
FIG. 10 is an exploded perspective view of a roller pair of the feed device.

As shown in FIGS. 9 and 10, the roller pair 102a comprises a first drive roller 128 and a first nip roller 130 movable toward and away from the first drive roller 128. The first drive roller 128 and the first nip roller 130 are rotatably supported on the fixed base 122. A first drive gear 132 and a first pulley 134 are coaxially coupled to the first drive roller 128. The first drive roller 128 has its axial length set to grip only the marginal edge Sa of the stimulable phosphor sheet S. The first driver roller 128 has a diameter which is the same as the pitch circle diameter of the first pulley 134.

The first nip roller 130 is fixed to an end of a rotatable shaft 136 which is longer than the width of the stimulable phosphor sheet S. The first nip roller 130 has its axial length set to grip only the marginal edge Sa of the stimulable phosphor sheet S. On one end of the rotatable shaft 136, there are disposed a spring 138 for normally urging the first nip roller 130 toward the first drive roller 128, and a first driven gear 140 held in mesh with the first drive gear 132.

On the other end of the rotatable shaft 136, there are coaxially disposed a first nip roller 130 and a gear 140. The first nip roller 130 is held in rolling contact with a first drive gear 128 by a spring 138. A gear 132 meshing with the gear 140 is coaxially fixed to the first drive roller 128.

The roller pair 100b comprises a second drive roller 142 and a second nip roller 144 which are rotatably supported on the movable base 124. A second drive gear 146 and a second pulley 148 are coaxially coupled to the second drive roller 142. The second drive roller 142 has a diameter which is the same as the pitch circle diameter of the second pulley 148.

As shown in FIG. 9, the second nip roller 144 and a second driven gear 152 are fixed to one end of a rotatable shaft 150, and the second driven gear 152 is held in mesh with the second drive gear 146. The second nip roller 144 is held in rolling contact with the second drive roller 142 by a spring 154. To the other end of the rotatable shaft 150, there are fixed a second nip roller 144 and a gear 152, with the second nip roller 144 being held in rolling contact with a second drive roller 142 by a spring 154. A gear 146 meshing with the gear 152 is coupled to the second drive roller 142.

As shown in FIGS. 7 through 9, the drive mechanism 126 comprises a single motor 160 mounted on the fixed base 122 and having a drive shaft 160a connected to a speed reducer 164 by a belt and pulley system 162. The speed reducer 164 has a drive pulley 166 held in mesh with a timing belt 168 which is also held in mesh with first and second pulleys 134, 148. The timing belt 168 extends between the first and second pulleys 134, 148 along the stimulable phosphor sheet S. The timing belt 168 has its outer surface operatively supported by a plurality of pulleys 170 mounted on the fixed base 122 and the movable base 124, and has its tension adjusted by a tension adjusting mechanism 172 when the movable base 124 is vertically moved.

The tension adjusting mechanism 172 has a frame 174 fixed to the movable base 124 and extending horizontally. The frame 174 has upper and lower guide bars 176a, 176b extending parallel to each other. On the guide bars 176a, 176b, there is mounted a movable belt end holder 178 for holding the end of the timing belt 168 as a loop. The movable belt end holder 178 comprises a slide base 180 movably engaging the guide bars 176a, 176b for movement therealong, and a pulley 182 rotatably supported in the slide base 180 and held in mesh with the timing belt 168.

A first wire 184, which has an end coupled to the slide base 180, is trained around rollers 186a, 186b supported on the frame 174 and extends parallel to the frame 174, with the opposite end connected to an end of a tension spring 188. The other end of the tension spring 188 is connected to an end of a second wire 190. The second wire 190 is trained around an upper movable roller 192 and a lower movable roller (first roller) 194, and extends upwardly. The second wire 190 is also trained around a fixed roller (second roller) 196 mounted on an upper portion of the fixed base 122, with the opposite end fixed to the upper portion of the fixed base 122 by a pin 198 (see FIG. 7).

Figure 11:
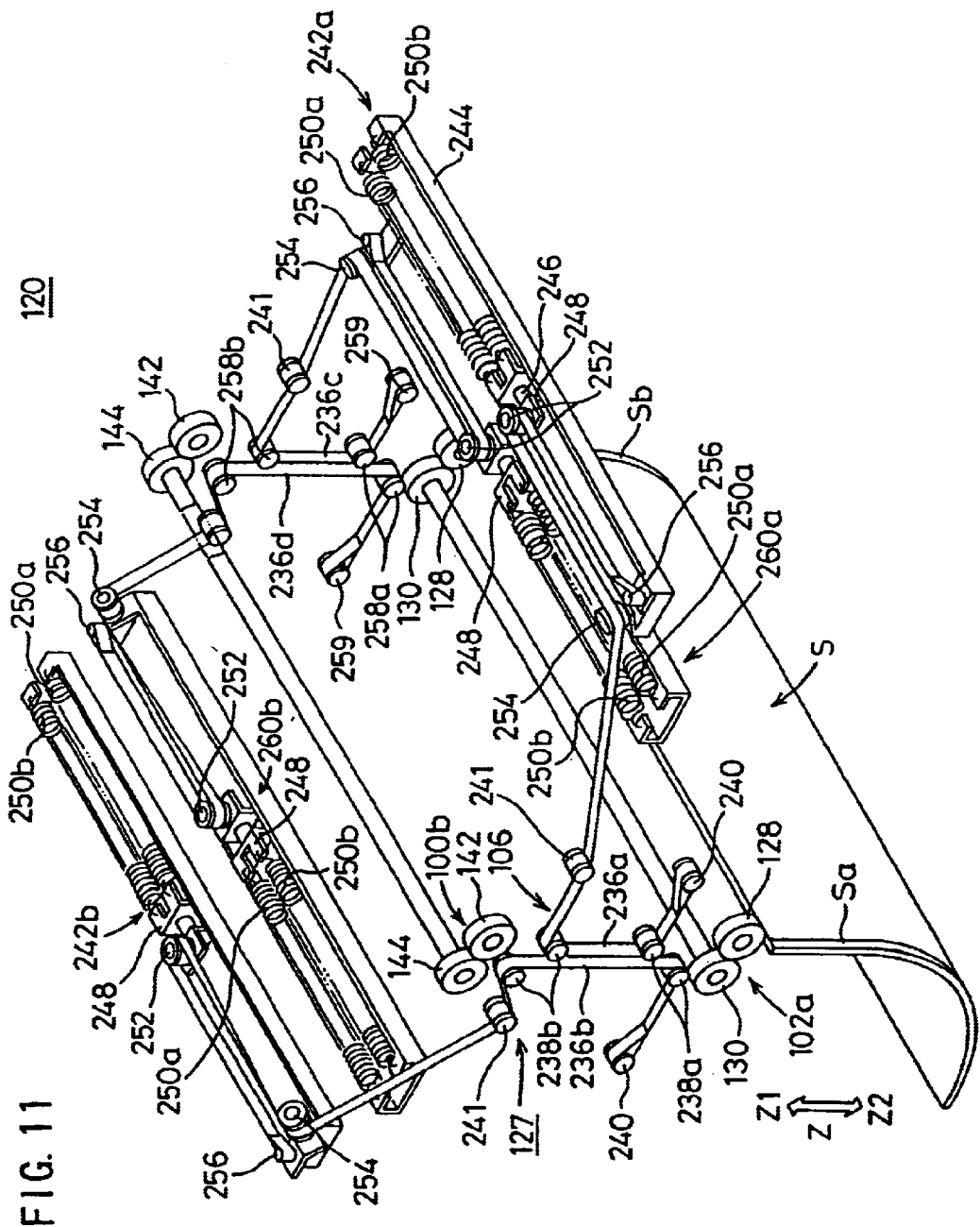
FIG. 11 is a perspective view of the feed device.
Figure 12:
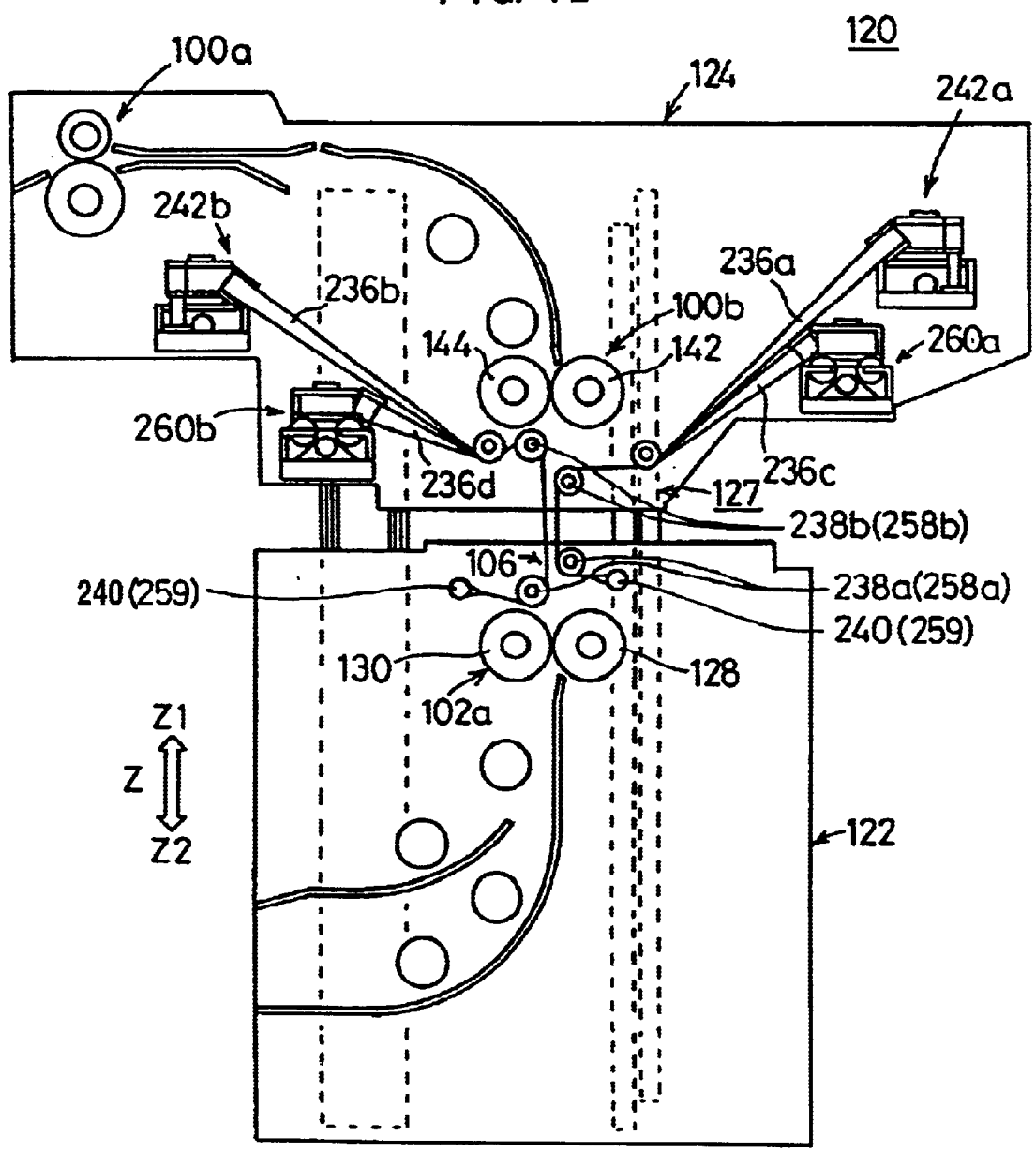
FIG. 12 is a side elevational view of the feed device.

As shown in FIGS. 6, 11, and 12, the guide mechanism 127 comprises guide members for holding the marginal edges Sa, Sb of the stimulable phosphor sheet S on its both surfaces, e.g., first through fourth tape members 236a–236d. The first and second tape members 236a, 236b, which guide the marginal edge Sa of the stimulable phosphor sheet S, extend vertically between the roller pairs 100b, 102a, thus serving as the vertical feed path 106. The first and second tape members 236a, 236b have respective lower ends engaged by respective guide rollers 238a and fixed to the fixed base 122 by respective fixing members 240.

The first and second tape members 236a, 236b are engaged by respective guide rollers 238b supported on the vertically movable base 38 below and closely to the roller pair 100b. The first and second tape members 236a, 236b have respective upper ends engaged by a plurality of guide rollers 241 mounted on the movable base 124 out of the vertical feed path 106, and also by respective first and second accommodating mechanisms 242a, 242b which accommodate the first and second tape members 236a, 236b while allowing them to be drawn out.

Figure 13:
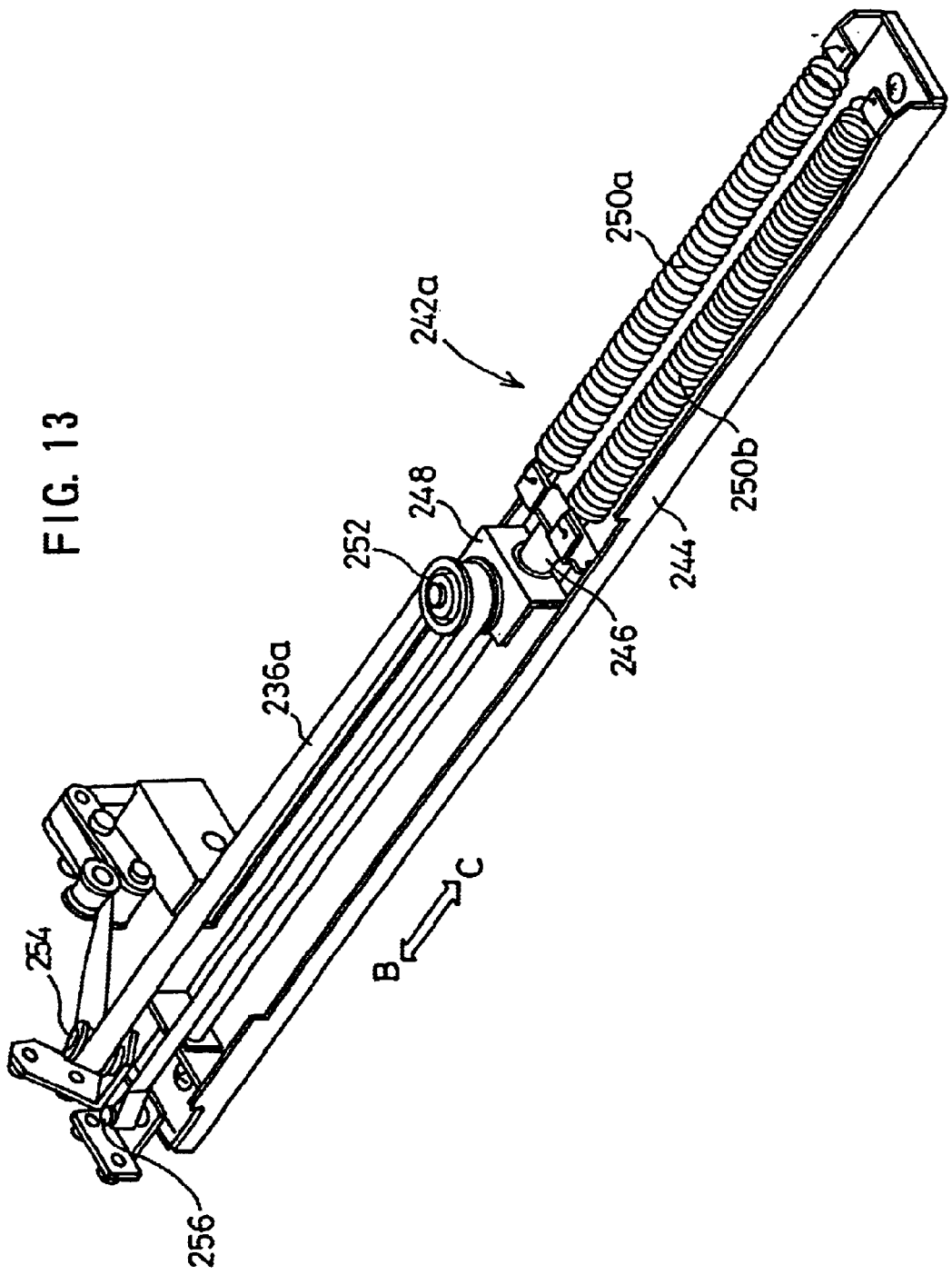
FIG. 13 is a perspective view of an accommodating mechanism of the feed device.

As shown in FIGS. 11 and 13, the first accommodating mechanism 242a has a frame 244 extending transversely across the stimulable phosphor sheet S and fixed to the movable base 124. A slide base 248 that is movable in the directions indicated by the arrows B, C along a guide rod 246 is mounted on the frame 244. Tension coil springs (resilient members) 250a, 250b have ends engaging the slide base 248 and opposite ends secured to an end of the frame 244.

A pulley 252 for supporting the first tape member 236a as a loop is rotatably supported on the slide base 248. On the end of the frame 244 remote from the tension coil springs 250a, 250b, there are mounted a roller 254 for causing the first tape member 236a to extend along the frame 244 via the pulley 252, and a fixing member 256 to which an end of the first tape member 236a extending along the frame 244 is fixed. The second accommodating mechanism 242b is identical in structure to the first accommodating mechanism 242a, and those parts of the second accommodating mechanism 242b which are identical to those of the first accommodating mechanism 242a are denoted by identical reference characters, and will not be described in detail below.

The third and fourth tape members 236c, 236d are disposed between the roller pairs 102a, 100b along the vertical feed path 106 by guide rollers 258a, 258b for guiding the marginal edge Sb of the stimulable phosphor sheet S. As shown in FIGS. 11 and 12, the third and fourth tape members 236c, 236d have respective lower ends fixed to fixing members 259 mounted on the fixed base 122, and respective upper ends accommodated by third and fourth accommodating mechanisms 260a, 260b fixedly mounted on the movable base 124. The third and fourth accommodating mechanisms 260a, 260b accommodate the third and fourth tape members 236c, 236d while allowing them to be drawn out. The third and fourth accommodating mechanisms 260a, 260b are identical in structure to the first and second accommodating mechanisms 242a, 242b and those parts of the third and fourth accommodating mechanisms 260a, 260b which are identical to those of the first and second accommodating mechanisms 242a, 242b are denoted by identical reference characters, and will not be described in detail below.

As shown in FIG. 2, three stimulable phosphor sheets S are present in the circulating feed system 86 at all times. These stimulable phosphor sheets S can be placed in three standby positions including a first standby position ST1 as a set position in the recording unit 80, a second standby position ST2 disposed in the horizontal feed path 108, and a third standby position ST3 disposed in the erasing assembly 84.

The reading unit 82 is positioned in the second casing 22. The reading unit 82 comprises an auxiliary scanning feed assembly 320 for feeding a stimulable phosphor sheet S in an auxiliary scanning direction which is a horizontal direction indicated by the arrow A, a laser beam radiating device 322 for applying a laser beam L as stimulating light substantially vertically to the stimulable phosphor sheet S as it is fed in the auxiliary scanning direction to scan the stimulable phosphor sheet S in a main scanning direction which is normal to the auxiliary scanning direction, and first and second light collecting systems 324, 326 for photoelectrically reading light that is emitted from the stimulable phosphor sheet S upon application of the laser beam L.

The auxiliary scanning feed assembly 320 has first and second roller pairs 328, 330 that are rotatable in synchronism with each other. The first light collecting system 324 comprises a first light guide 332a having an end which is disposed at a position where the laser beam L is applied to a recording surface of the stimulable phosphor sheet S and extends in the main scanning direction, and a first photomultiplier 334a mounted on the other end of the first light guide 332a. The second light collecting system 326 comprises a second light guide 332b having an end which is disposed on the side of the reverse surface of the stimulable phosphor sheet S and extends in the main scanning direction, and a second photomultiplier 334b mounted on the other end of the second light guide 332b.

The erasing assembly 84 comprises a first erasing unit 340a disposed over the recording surface of the stimulable phosphor sheet S and a second erasing unit 340b disposed over the reverse surface of the stimulable phosphor sheet S. The first and second erasing units 340a, 340b have respective erasing light sources 342a, 342b.

As shown in FIG. 1, the controller 24 has a control panel 354 which has a plurality of lamps 350, a display panel 352, and a plurality of lamps 353 for indicating a recording size with selector keys. When the controller 24 is turned on by the operator who operates a console (not shown) or a recording size is selected, the lamps 350, 353 indicate such turn-on and recording size information, and the display unit 352 displays the ID number and name of a patient registered via the console or a recording menu.

The switch unit 26 has a first foot switch 360 for unlocking the top panel 52 of the imaging bed 16 for horizontal movement thereof, a second foot switch 362 for lowering the imaging bed 16, a third foot switch 364 for lifting the imaging bed 16, and a fourth foot switch 366 for stopping the imaging bed 16 against vertical movement in case of emergency. The fourth foot switch 366 has a pedal cover 368. When a release button 370 in the pedal cover 368 is manually turned in a predetermined direction, the imaging bed 16 is allowed to move vertically.

An X-ray radiating unit 372 is positioned over the top panel 52.

Operation of the image information reading apparatus 10 thus constructed will be described below.

An ID card carrying ID information of a patient, including an ID number and a name, is prepared, and read by the console (not shown). The console selects an imaging area, such as a chest or an abdomen, of the patient, and a recording menu. Then, a recording size is selected, if necessary. Then, the patient as a subject to be imaged is placed on the imaging bed 16.

At this time, the vertical position of the imaging bed 16 in the direction indicated by arrow Z is adjusted depending on the condition of the patient, the height of the patient, and the carriage, such as a wheelchair, a stretcher, or the like, by which the patient has been carried. Specifically, the operator presses the second foot switch 362 to cause the hydraulic unit 46 of the lifting/lowering mechanism 18 to operate the hydraulic cylinders 40a, 40b (see FIG. 3). The rods 42a, 42b of the hydraulic cylinders 40a, 40b are retracted to swing the second swing arms 34a, 34b, which are coupled to the rods 42a, 42b by the attachment 44a, 44b, downwardly about the pivot shafts 32a, 32b.

Since the first swing arms 30a, 30b are coupled to the second swing arms 34a, 34b by the joint shafts 36a, 36b, when the second swing arms 34a, 34b are turned downwardly, the first swing arms 30a, 30b are angularly moved downwardly about the pivot shafts 28a, 28b. Therefore, the vertically movable base 38 is moved downwardly to lower the imaging bed 16.

When the operator presses the third foot switch 364, the hydraulic unit 46 actuates the hydraulic cylinders 40a, 40b in the opposite direction. Therefore, the vertically movable base 38 supported by the first swing arms 30a, 30b and the second swing arms 34a, 34b is elevated, thus lifting the imaging bed 16.

In this manner, the imaging bed 16 is adjusted to a vertical position where the patient can easily be placed onto the top panel 52. After the patient is placed on the top panel 52 with the back or one side down, the operator selectively presses the second foot switch 362 or the third foot switch 364 to adjust the vertical position of the top panel 52 for easy subsequent imaging operation. The operator further presses the first foot switch 360 or continuously turns on one of the touch switches 66 on the top panel 52 to energize the electromagnetic brakes 74a–74d of the first and second lock units 68, 70, thereby making the pinion gears 76a–76d free to rotate. The movable table 50 and the top panel 52 are now unlocked.

Figure 14:
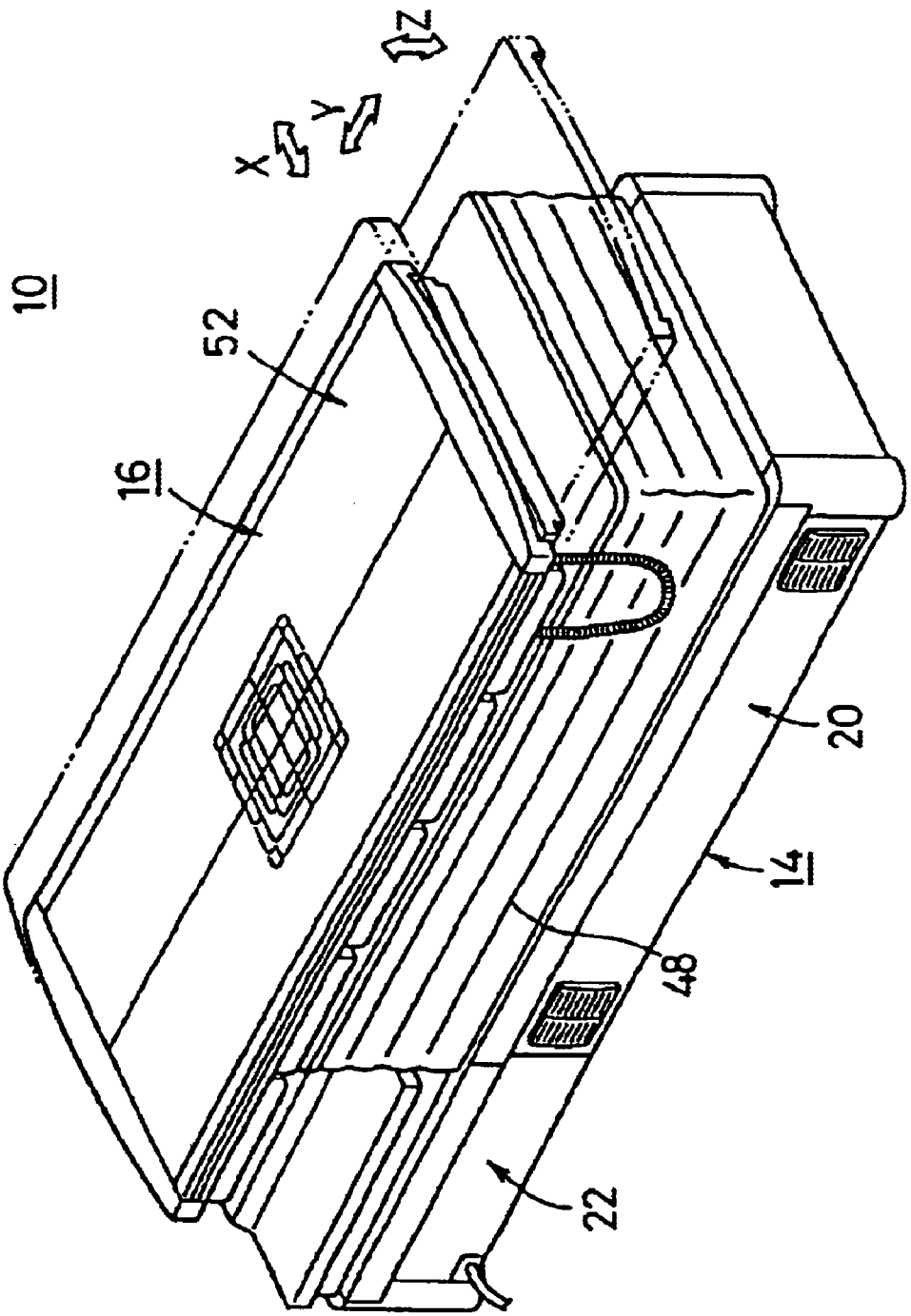
FIG. 14 is a perspective view showing the manner in which the imaging bed operates.

With the touch switch 66 being continuously pressed, the operator slides the top panel 52 in the directions indicated by the arrows X, Y to adjust the height position of the patient until the imaging area of the patient enters a radiating range of the X-ray radiating unit 372 (see FIG. 14). After the imaging area of the patient is positioned, the operator releases the touch switch 66 to de-energize the electromagnetic brakes 74a–74d, whereupon the movable table 50 and the top panel 52 are locked.

The X-ray radiating unit 372 is then energized to record radiation image information of the patient on a stimulable phosphor sheet S in the recording unit 80. At this time, the other two stimulable phosphor sheets S are placed in the second and third standby positions ST2, ST3, respectively.

When the roller pair 100a of the circulating feed system 86 is rotated, the stimulable phosphor sheet S which has recorded the radiation image information is gripped at its marginal edges Sa, Sb by the roller pair 100a and removed from the recording unit 80. The stimulable phosphor sheet S is then gripped by the roller pairs 100b, 102 and transferred from the vertical feed path 106 into the horizontal feed path 108 (see FIG. 6). Then, the stimulable phosphor sheet S is fed from the first casing 20 into the second casing 22 by the roller pairs 102, and turned 180° above the horizontal feed path 108 by the roller pair 104 and fed into the auxiliary scanning feed assembly 320 of the reading unit 82.

In the auxiliary scanning feed assembly 320, the first and second roller pairs 328, 330 are synchronously rotated by a motor (not shown). The stimulable phosphor sheet S is gripped at its marginal edges Sa, Sb by the first and second roller pairs 328, 330 and fed in the auxiliary scanning direction indicated by the arrow A. At this time, the laser beam L is emitted from the laser beam radiating device 322 and applied to the recording surface of the stimulable phosphor sheet S to scan the stimulable phosphor sheet S in the main scanning direction.

When irradiated by the laser beam L, the recording surface of the stimulable phosphor sheet S emits light which represents the recorded radiation image information. The emitted light is photoelectrically read by the first light collecting system 324. Light that has passed through a transparent base of the stimulable phosphor sheet S is emitted from the reverse surface thereof, and photoelectrically read by the second light collecting system 326.

The stimulable phosphor sheet S, from which the recorded radiation image information has been read, is fed from the second casing 22 back into the first casing 20, and delivered along the inclined feed path 110 into the erasing assembly 84. In the erasing assembly 84, the erasing light sources 342a, 342b of the first and second erasing units 340a, 340b apply erasing light to the both surfaces of the stimulable phosphor sheet S to erase unwanted remaining radiation image information from the stimulable phosphor sheet S.

After the remaining radiation image information has been erased from the stimulable phosphor sheet S, the stimulable phosphor sheet S is turned 180° below the inclined feed path 110 and delivered into the switchback feed path 112. The roller pair 114 on the switchback feed path 112 is reversed to feed the stimulable phosphor sheet S from the switchback feed path 112 into the vertical feed path 106, along which the stimulable phosphor sheet S is delivered by the roller pairs 100a, 100b into the recording unit 80.

In the present embodiment, the imaging bed 16 with the top panel 52 for supporting the patient with the back or one side down is vertically movable with respect to the housing 14 on the floor 12 by the lifting/lowering mechanism 18. Therefore, when the patient is to be placed onto the top panel 52, the vertical position of the imaging bed 16 is adjusted depending on the condition of the patient, the height of the patient, and the carriage, such as a wheelchair, a stretcher, or the like, by which the patient has been carried.

Even if the patient is of a small height, the operator is not required to use a step, and can easily and smoothly transfer the patient from a wheelchair or a stretcher to the top panel 52. As a consequence, the operator can efficiently place the patient onto or off the top pale 52, with a greatly reduced physical and mental burden on the patient or the operator or both.

After the patient has been placed on the top panel 52, the operator can operate the lifting/lowering mechanism 18 to adjust the imaging bed 16 to a vertical position for easy imaging operation. The operator can thus move the top panel 52 at the desired vertical position in desired horizontal directions, and finds it efficient to operate the top panel 52.

The switch unit 26 includes the second foot switch 362 for lowering the imaging bed 16 and the third foot switch 364 for lifting the imaging bed 16. By using the second and third switches 362, 364, the operator can lift or lower the imaging bed 16 without using the hands.

The switch unit 26 also has the fourth foot switch 366 for stopping the imaging bed 16 against vertical movement in case of emergency. If a malfunction occurs while the imaging bed 16 is being lifted or lowered, the operator presses the fourth foot switch 366 to stop the imaging bed 16 against further vertical movement for quickly and reliably avoiding any possible damage to the image information reading apparatus 10. To unlock the imaging bed 16, the operator turns the pedal cover 368 and then turns the release button 370 clockwise for thereby allowing the imaging bed 16 to move vertically.

Figure 15:
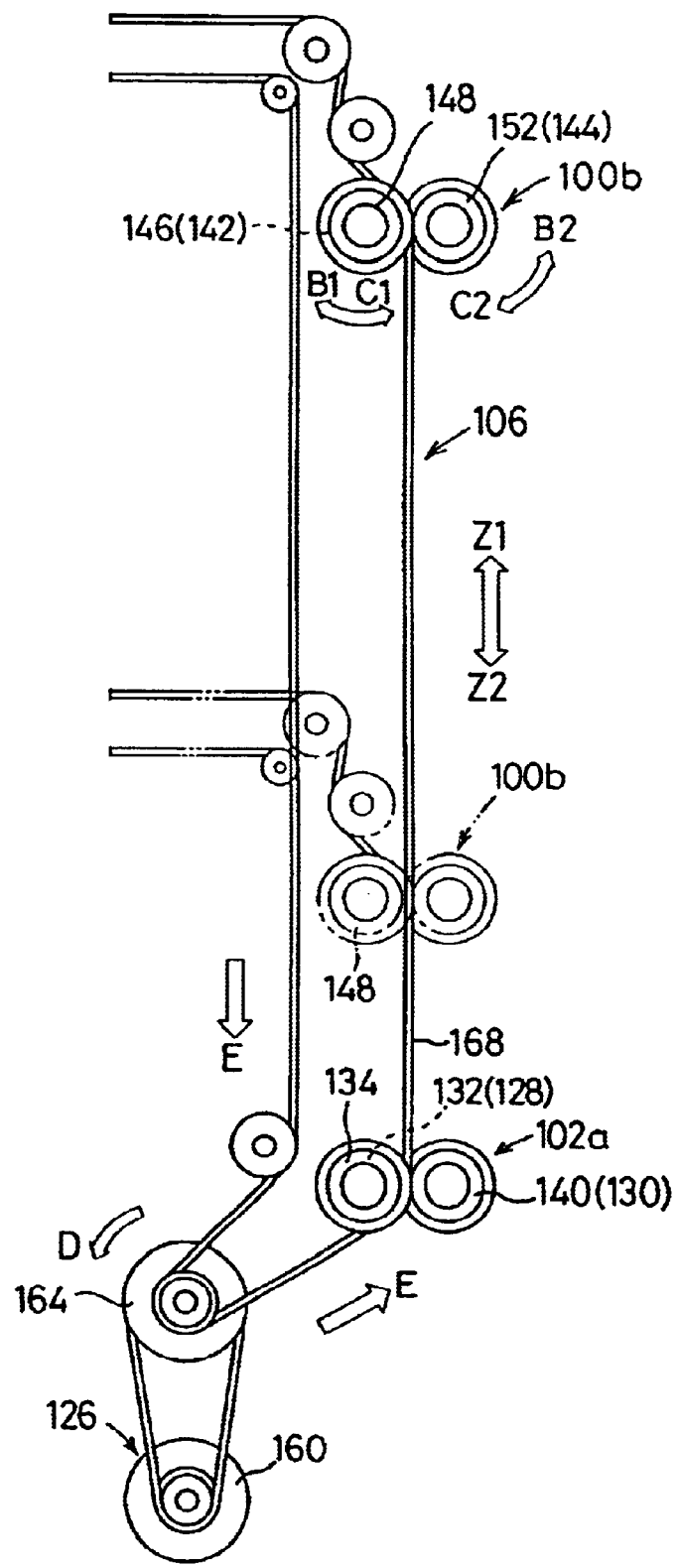
FIG. 15 is a perspective view showing the manner in which the feed device operates.

In the present embodiment, when the imaging bed 16 is vertically moved to extend or contract the length of the vertical feed path 106, it is possible to feed a stimulable phosphor sheet S in the housing 14. Specifically, as shown in FIG. 15, when the imaging bed 16 is lifted, the roller pair 100b mounted on the movable base 124 moves upwardly in the direction indicated by the arrow Z1. To the second drive roller 142 of the roller pair 100b, there is coupled the second pulley 148 that is held in mesh with the timing belt 168.

The first pulley 134 held in mesh with the timing belt 168 is coupled to the first drive roller 128 of the roller pair 102a. The motor 160 coupled to the speed reducer 164 is positioned near the roller pair 102a. The load on the roller pair 102a is set to a value greater than the load on the roller pair 100b. Therefore, when the roller pair 100b moves in the direction indicated by the arrow Z1, the second pulley 148 of the roller pair 100b rotates in the direction indicated by the arrow B1 along the timing belt 168.

The second drive gear 146 is coupled to the second drive roller 142, and the second nip roller 144 held in mesh with the second drive gear 146 is rotated in the direction indicated by the arrow B2 by the second driven gear 152. As shown in FIG. 9, the second nip roller 144 is fixed to one end of the rotatable shaft 150, and the other second nip roller 144 is fixed to the other end of the rotatable shaft 150. The second nip roller 144 and the second drive roller 142 are rotated by the gears 152, 146 in the same direction as the other second nip roller 144 and the other second drive roller 142.

When the roller pair 100b is displaced downwardly in the direction indicated by the arrow Z2 in FIG. 15, the second pulley 148 is rotated in the direction indicated by the arrow C1 along the timing belt 168, and the second nip roller 144 is rotated in the direction indicated by the arrow C2.

In the present embodiment, as described above, the load on the roller pair 102a is set to a value greater than the load on the roller pair 100b, and the timing belt 168 and the second pulley 148 function as a rack and a pinion. Therefore, when the movable base 124 is vertically moved, the second drive roller 142 and the second nip roller 144 are rotated automatically an angular interval corresponding to the distance that the roller pair 100b is displaced.

The diameter of the second drive roller 142 has is the same as the pitch circle diameter of the second pulley 148. Consequently, the distance that the roller pair 100b is displaced is equal to the distance that the stimulable phosphor sheet S is fed by the rotation of the roller pair 100b. When the roller pair 100b is vertically moved with the motor 160 being de-energized, the roller pair 100b rolls on the stimulable phosphor sheet S, which is not vertically moved.

As shown in FIG. 15, when the speed reducer 164 is rotated in the direction indicated by the arrow D by the motor 160, the timing belt 168 cyclically runs in the direction indicated by the arrow E, causing the rollers 102a, 100b to feed the stimulable phosphor sheet S along the vertical feed path 106 in the direction indicated by the arrow Z1. If the imaging bed 16 is lifted in the direction indicated by the arrow Z1 at this time, then the roller pair 100b is displaced from the two-dot-and-dash-line position to the solid-line position in FIG. 15, increasing the feed path between the roller pair 100b and the roller pair 102a.

Since the timing belt 168 runs in the direction indicated by the arrow E, the second drive roller 142 of the roller pair 100b and the first drive roller 128 of the roller pair 102a rotate synchronously with each other in the direction indicated by the arrow C1. When the roller pair 100b moves in the direction indicated by the arrow Z1, the second pulley 148 rotates in the direction indicated by the arrow B1 with respect to the timing belt 168, reducing the speed at which the second drive roller 142 rotates in the direction indicated by the arrow C1.

Therefore, the rotational speed of the second drive roller 142 is reduced in a manner commensurate with the speed that the roller pair 100b is displaced, so that there is developed no speed difference between the roller pair 102a and the roller pair 100b. While the imaging bed 16 is being vertically displaced, it is thus possible to transfer the stimulable phosphor sheet S smoothly and reliably from the roller pair 102a to the roller pair 100b. As a result, the image information reading apparatus 10 operates efficiently.

The drive mechanism 126 is required to have the single motor 160 as its actuator. Therefore, the drive mechanism 126 is relatively simple in structure, and the rotational speed of the roller pair 100b is synchronized with the speed that the roller pair 100b is displaced, by the simple mechanical arrangement provided by the timing belt 168 and the second pulley 148 which serve as a rack and a pinion. It is not necessary to employ a sensor for detecting the speed at which the roller pair 100b moves and a complex control system for controlling the roller pair 100b.

As shown in FIG. 15, when the roller pair 100b moves downwardly in the direction indicated by the arrow Z2 while the timing belt 168 is cyclically running in the direction indicated by the arrow E, the second pulley 148 rotates in the direction indicated by the arrow C1 with respect to the timing belt 168, increasing the rotational speed of the second drive roller 142. The rotational speed of the roller pair 100b is thus equalized to the rotational speed of the roller pair 102a, making it possible to transfer the stimulable phosphor sheet S smoothly and reliably from the roller pair 102a to the roller pair 100b.

When the stimulable phosphor sheet S is removed from the recording unit 80 and fed to the reading unit 82, the timing belt 168 cyclically runs in the direction opposite to the direction indicated by the arrow E. Therefore, even when the imaging bed 16 is vertically moved, the stimulable phosphor sheet S can be transferred smoothly and reliably from the roller pair 100b to the roller pair 102a.

Figure 16:
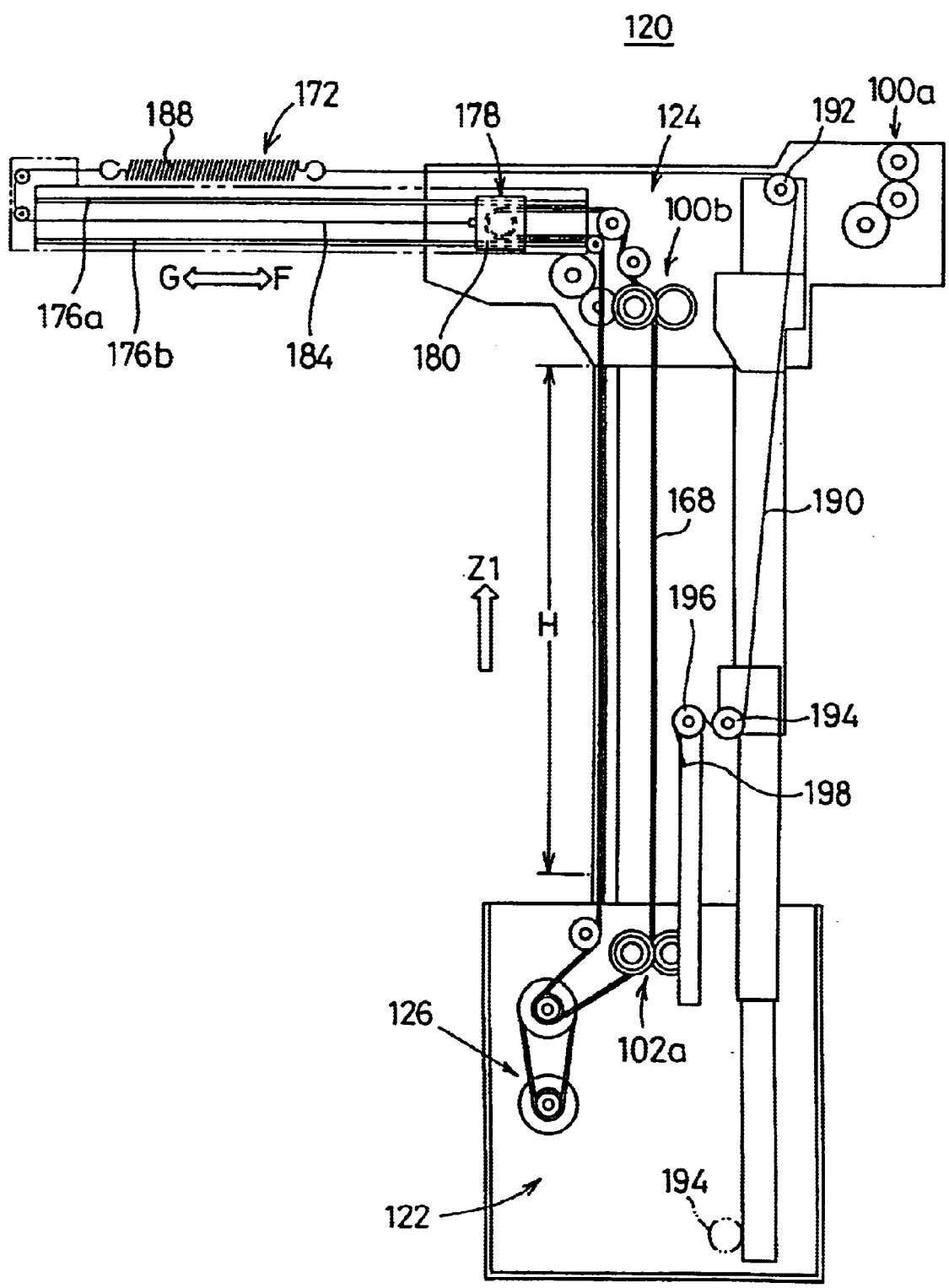
FIG. 16 is a side elevational view showing a movable base of the feed device which is elevated.

In the present embodiment, the tension adjusting mechanism 172 prevents the timing belt 168 from being tensioned to an undesirably large level when the imaging bed 16 is vertically moved a relatively large distance. Specifically, as shown in FIG. 16, when the movable base 124 moves a distance H upwardly in the direction indicated by the arrow Z1, the slide base 180 of the movable belt end holder 178 which holds the end of the timing belt 168 as a loop is pulled toward the roller pair 100b in the direction indicated by the arrow F.

When the lower movable roller 194 on the movable base 124 moves in the direction indicated by the arrow Z1, the second wire 190 trained around the lower movable roller 194 is paid out a length 2H in the direction indicated by the arrow Z1. Based on the length 2H of the second wire 190, the slide base 180 is displaced the distance H in the direction indicated by the arrow F. The spring 188 which engages the slide base 180 via the first wire 184 is displaced the distance H in the direction indicated by the arrow G which is opposite to the direction indicated by the arrow F.

Consequently, irrespective of the position of the movable base 124 between the lowermost position and the uppermost position thereof, the tension of the timing belt 168 under the bias of the spring 188 is maintained at a constant level at all times. Thus, the service life of the timing belt 168 is prevented from being shortened. Even when the movable base 124 is displaced a considerably large distance, the spring 188 is not unduly pulled, but can keep the timing belt 168 under constant tension. In addition, the tension adjusting mechanism 172 is relatively simple in its overall structure.

Figure 17:
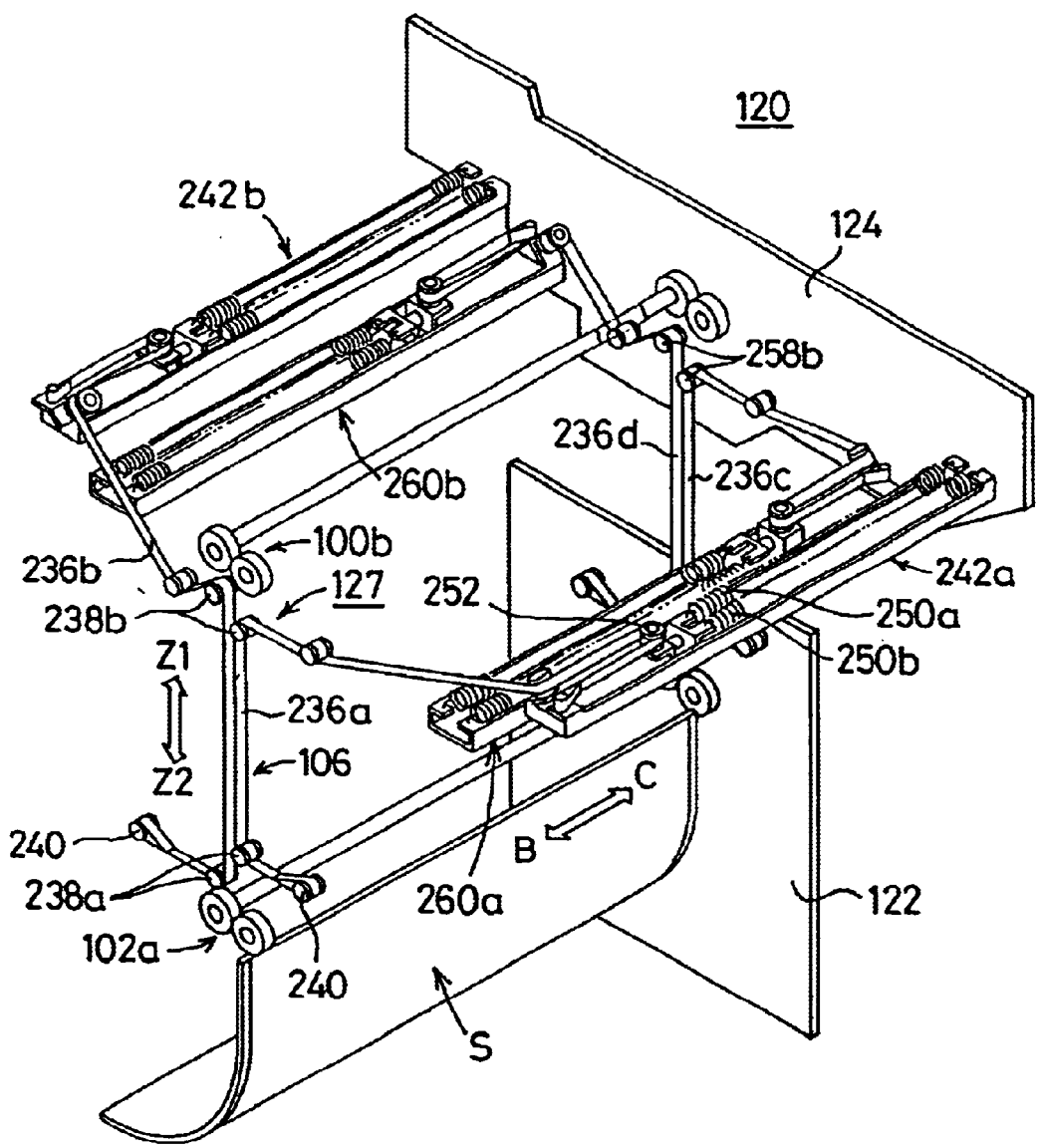
FIG. 17 is a perspective view showing the manner in which the feed device operates.
Figure 18:
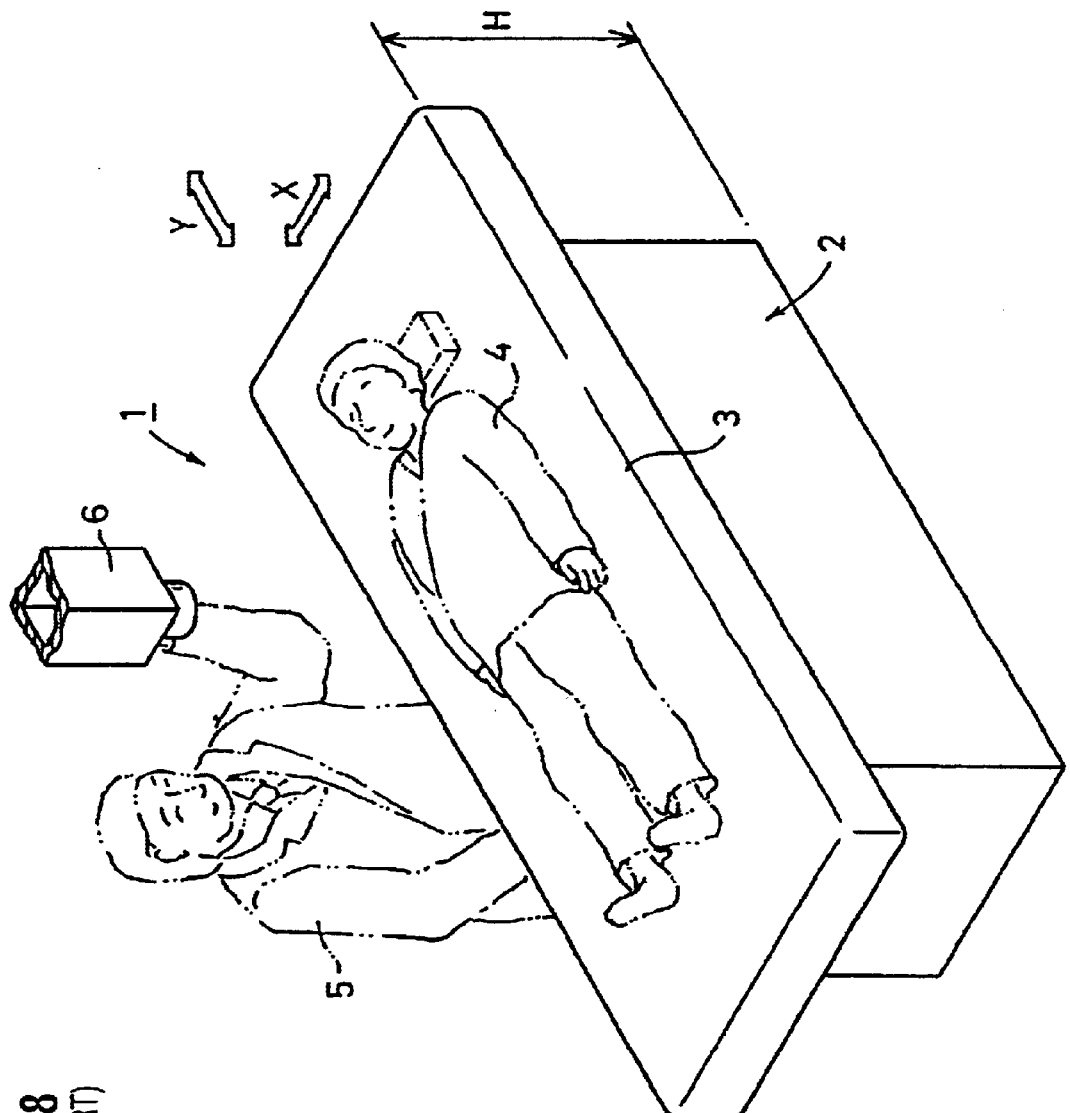
FIG. 18 is a perspective view of a conventional radiation image information reading apparatus.

As shown in FIG. 17, when the movable base 124 moves in the direction indicated by the arrow Z1, since the first and second tape members 236a, 236b has their lower ends fixed to the fixed base 122 by the respective fixing members 240, the first and second tape members 236a, 236b are paid out from the first and second accommodating mechanisms 242a, 242b mounted on the movable base 124 toward the roller pair 102a. In the first and second accommodating mechanisms 242a, 242b, as shown in FIG. 11, the first and second tape members 236a, 236b are supported as loops by the pulleys 252, with their ends fixed to the fixing members 256.

Therefore, when the movable base 124 moves in the direction indicated by the arrow Z1, tensile forces act on the pulleys 252 in the direction indicated by the arrow B, moving the pulleys 252 in the direction indicated by the arrow B against the resilient forces of the coil springs 250a, 250b. The first and second tape members 236a, 236b are now paid out from the first and second accommodating mechanisms 242a, 242b. Even if the movable base 124 moves a large distance in the direction indicated by the arrow Z1, the first and second tape members 236a, 236b are placed between the roller pairs 100b, 102a by being supported by the guide rollers 238a, 238b. Therefore, the marginal edge Sa of the stimulable phosphor sheet S is smoothly and reliably guided by the roller pairs 100b, 102a, allowing the stimulable phosphor sheet S to be fed stably.

When the movable base 124 moves in the direction indicated by the arrow Z1, the third and fourth tape members 236c, 236d are also paid out a length commensurate with an increase in the feed path between the guide rollers 258a, 258b for smoothly feeding the marginal edge Sb of the stimulable phosphor sheet S in a similar manner to the first and second tape members 236a, 236b.

When the movable base 124 moves downwardly in the direction indicated by the arrow Z2, the guide roller 238b is displaced toward the guide roller 238a, causing the first and second tape members 236a, 236b to produce respective excess lengths between the guide rollers 238a, 238b. At this time, in the first and second accommodating mechanisms 242a, 242b which accommodate the first and second tape members 236a, 236b, the pulleys 252 are displaced in the direction indicated by the arrow C by the coil springs 250a, 250b engaging the pulleys 252. Therefore, the excess lengths of the first and second tape members 236a, 236b are absorbed by the first and second accommodating mechanisms 242a, 242b.

Consequently, even when the movable base 124 is displaced to its lowermost position, the first and second tape members 236a, 236b are prevented from being unduly slackened between the guide rollers 238a, 238b, and are capable of reliably guiding the marginal edge Sa of the stimulable phosphor sheet S. Similarly, when the movable base 124 moves downwardly in the direction indicated by the arrow Z2, the third and fourth tape members 236c, 236d are prevented from being slackened between the guide rollers 258a, 258b, and are capable of reliably guiding the marginal edge Sb of the stimulable phosphor sheet S.

As described above, when the movable base 124 is placed in any desired vertical position, the first through fourth tape members 236a through 236d are reliably positioned between the roller pairs 100b, 102a for thereby effectively preventing the stimulable phosphor sheet S from failing to be fed due to an insufficient guiding length. Even when the movable base 124 is displaced upwardly a large distance, the stimulable phosphor sheet S can be fed stably between the roller pairs 100b, 102a, and the guide mechanism 127 is effectively simplified in structure.

The guide mechanism 127 only needs to be provided with the first through fourth tape members 236a through 236d that can be extended and contracted along the vertical feed path 106, and hence can be manufactured economically. The first through fourth tape members 236a through 236d may be made of synthetic resin or very thin sheet metal.

The first through fourth accommodating mechanisms 242a, 242b, 260a, 260b have the respective pulleys 252 for supporting the first through fourth tape members 236a through 236d as loops. When the movable base 124 moves the distance H upwardly in the direction indicated by the arrow Z1, the pulleys 252 are displaced the distance H/2 in the direction indicated by the arrow B. Therefore, even when the distance that the movable base 124 is displaced is considerably large, the first through fourth accommodating mechanisms 242a, 242b, 260a, 260b have their longitudinal dimensions greatly reduced. As a consequence, the overall size of the feed device 120 is reduced, and the first through fourth tape members 236a through 236d are reliably prevented from being unduly tensioned.

The built-in radiation image information reading apparatus 10 with stimulable phosphor sheets S being circulated in the housing 14 has been described above. However, the principles of the present invention are not limited to the illustrated details. Sheets to be fed may include photographic photosensitive films on which images are directly recorded. The principles of the present invention are also applicable to various feed devices in which the length of a feed path between roller pairs for gripping and feeding such sheet-like members is variable.

In the image scanning apparatus according to the present invention, the imaging bed for supporting the patient, with the back or one side down, thereon can be vertically moved with respect to the housing by the lifting/lowering mechanism. By adjusting the vertical position of the imaging bed, the subject can easily and smoothly be placed onto the imaging bed and the imaging bed can easily and smoothly be handled, so that the image scanning apparatus can be operated with ease.

When the movable roller pair is displaced toward and away from the fixed roller pair, the second pulley of the movable roller pair is rotated along the timing belt, taking up a speed difference between the movable roller pair and the fixed roller pair due to the movement of the movable roller pair. Therefore, even while the movable roller pair is moving, the sheet can be transferred smoothly and reliably between the movable roller pair and the fixed roller pair. In addition, the feed device is relatively simple in structure.

When the length of the feed path for feeding the sheet is varied, the guide members for guiding the sheet are extended or contracted depending on the change in the length of the feed path. Therefore, the sheet can smoothly be fed stably and efficiently without fail.

Although a certain preferred embodiment of the present invention has been shown and described in detail, it should be understood that various changes and modifications may be made therein without departing from the scope of the appended claims.

What is claimed is:

1. An image scanning apparatus for gripping and feeding a scanned body with roller pairs which are spaced apart from each other by a variable distance, comprising:
   a fixed base fixedly mounted in said housing;
   a fixed roller pair rotatably supported on said fixed base and including a first drive roller;
   a movable base movable with respect to said fixed base;
   a movable roller pair rotatably supported on said movable base and spaced a variable distance from said fixed roller pair, said movable roller pair including a second drive roller;
   a drive mechanism for rotating said fixed roller pair and said movable roller pair in unison with each other;
   said drive mechanism comprising:
      a single motor;
      a first pulley coupled to said first drive roller
      a second pulley coupled to said second drive roller and having a pitch circle diameter which is the same as the diameter of said second drive roller; and
      a timing belt operatively connected to said motor and held in mesh with said first pulley and said second pulley, for rotating only said second pulley when said movable base moves toward and away from said fixed base with said motor de-energized; and
   a tension adjusting mechanism for adjusting tension of said timing belt, said tension adjusting mechanism comprising
      movable belt end holding means mounted on said movable base for holding an end of said timing belt as a loop;
      a first wire having an end coupled to said movable belt end holding means and an opposite end coupled to a tension spring; and
      a second wire having an end coupled to a tension spring, trained around a first roller mounted on a lower portion of said movable base and a second roller mounted on an upper portion of said fixed base, and having an opposite end fixed to said fixed base;
   the arrangement being such that said first roller moves closely to said second roller when said movable base moves away from said fixed base.

2. The image scanning apparatus according to claim 1, further comprising:
   an imaging bed for placing a subject thereon, said imaging bed having a recording unit for temporarily recording radiation image information of the subject on a stimulable phosphor sheet;

a housing accommodating therein a reading unit for applying stimulating light to the stimulable phosphor sheet with the radiation image information recorded thereon to photoelectrically read the radiation image information from said stimulable phosphor sheet, and an erasing assembly for erasing remaining radiation image information from the stimulable phosphor sheet after the recorded radiation image information is read from the stimulable phosphor sheet; and a lifting/lowering mechanism mounted in said housing for lifting and lowering said imaging bed with respect to said housing.

3. An image scanning apparatus according to claim 2, further comprising:

a lifting foot switch for lifting said imaging bed;

a lowering foot switch for lowering said imaging bed; and an emergency foot switch for stopping said imaging bed in case of emergency.

4. An image scanning apparatus according to claim 3, further comprising a switch unit, wherein said lifting foot switch, said lowering foot switch, and said emergency foot switch are assembled together in said switch unit.

5. An image scanning apparatus according to claim 2, wherein said timing belt extends between said first pulley and said second pulley along said stimulable phosphor sheet.

6. An image scanning apparatus according to claim 2, further comprising:

a guide mechanism for guiding said stimulable phosphor sheet along a feed path;

said guide mechanism comprising:

a plurality of guide members extensible and contractible depending on a change in the length of said feed path when said feed path extends and contracts.

7. An image scanning apparatus according to claim 6, wherein said guide members comprise a plurality of tape members for holding at least one surface of said stimulable phosphor sheet, further comprising:

a plurality of accommodating mechanisms for accommodating ends of said tape members, respectively, out of said feed path while allowing said tape members to be drawn out.

8. An image scanning apparatus according to claim 7, wherein said accommodating mechanisms comprise:

pulleys for supporting the ends of said tape members, respectively, as loops; and resilient members for pulling said pulleys to tension said tape members.

9. An image scanning apparatus according to claim 7, wherein said tape members comprise first through fourth tape members for holding opposite marginal edges of said stimulable phosphor sheet from opposite surfaces thereof, and said accommodating mechanisms comprise first through fourth accommodating mechanisms for accommodating said first through fourth tape members, respectively.

10. An image scanning apparatus according to claim 1, wherein said timing belt extends between said first pulley and said second pulley along said scanned body.

11. The image scanning apparatus according to claim 2, wherein said imaging bed comprises a top panel for placing the subject thereon, said top panel being movable horizontally along two axes extending perpendicularly to each other.

12. An image scanning apparatus according to claim 11, wherein said imaging bed further comprises:

lock means for locking said top panel in a selected position; and a switch mounted on said top panel for unlocking said top panel from said lock means.

13. An image scanning apparatus having an extensible and contractible feed path for feeding a scanned body therealong, comprising:

a guide mechanism for guiding said scanned body along the feed path;

said guide mechanism comprising:

a plurality of guide members extensible and contractible depending on a change in the length of said feed path when said feed path extends and contracts;

wherein said guide members comprise a plurality of tape members for holding at least one surface of said scanned body; and a plurality of accommodating mechanisms for accommodating ends of said tape members, respectively, out of said feed path while allowing said tape members to be drawn out; and wherein said accommodating mechanisms comprise pulleys for supporting the ends of said tape members, respectively, as loops; and resilient members for pulling said pulleys to tension said tape members.

14. An image scanning apparatus according to claim 13, wherein said scanned body comprises a stimulable phosphor sheet, said tape members comprising first through fourth tape members for holding opposite marginal edges of said stimulable phosphor sheet from opposite surfaces thereof, and said accommodating mechanisms comprise first through fourth accommodating mechanisms for accommodating said first through fourth tape members, respectively.

* * * * *